US012668836B2

(12) United States Patent
Gerber et al.

(10) Patent No.: US 12,668,836 B2
(45) Date of Patent: Jun. 30, 2026

(54) DETECTION OF RECOMBINASE POLYMERASE AMPLIFICATION (RPA) AMPLICONS VIA FEN1 CLEAVAGE

(71) Applicant: TETRACORE, INC., Rockville, MD (US)

(72) Inventors: Kyle Gerber, Rockville, MD (US); Lisa Cockrell, Centreville, VA (US); William Nelson, Rockville, MD (US); Kyle Armantrout, Los Angeles, CA (US)

(73) Assignee: TETRACORE, INC., Rockville, MD (US)

( * ) Notice: Subject to any disclaimer, the term of this patent is extended or adjusted under 35 U.S.C. 154(b) by 426 days.

(21) Appl. No.: 17/327,144

(22) Filed: May 21, 2021

(65) Prior Publication Data

US 2022/0372564 A1     Nov. 24, 2022

(51) Int. Cl.
*C12Q 1/68* (2018.01)
*B01L 3/00* (2006.01)
*C12Q 1/6848* (2018.01)

(52) U.S. Cl.
CPC ........ *C12Q 1/6848* (2013.01); *B01L 3/50273* (2013.01); *B01L 2400/0633* (2013.01)

(58) Field of Classification Search
None
See application file for complete search history.

(56) References Cited

U.S. PATENT DOCUMENTS

| 4,615,341 A | 10/1986 | Marzolf et al. |
| 5,223,414 A | 6/1993 | Zarling et al. |
| 5,670,316 A | 9/1997 | Sena et al. |

| 5,869,003 A | * | 2/1999 | Nason | G01N 1/02 |
| | | | | 422/430 |
| 5,879,635 A | | 3/1999 | Nason | |
| 7,270,981 B2 | | 9/2007 | Armes et al. | |
| 7,666,598 B2 | | 2/2010 | Piepenburg et al. | |
| 7,763,427 B2 | | 7/2010 | Piepenburg et al. | |
| 10,758,908 B2 | | 9/2020 | Nelson et al. | |
| 11,149,320 B1 | * | 10/2021 | Brambati | C12Q 1/70 |
| 2002/0136665 A1 | | 9/2002 | Hayton et al. | |
| 2007/0054296 A1 | * | 3/2007 | Piepenburg | C12Q 1/6853 |
| | | | | 435/6.13 |

(Continued)

FOREIGN PATENT DOCUMENTS

| WO | WO-2017046192 A1 * | 3/2017 | ............... | C12Q 1/68 |

OTHER PUBLICATIONS

NCBI Accession No. MN975262 (Feb. 11, 2020).*

(Continued)

*Primary Examiner* — Aaron A Priest

(74) *Attorney, Agent, or Firm* — Finnegan, Henderson, Farabow, Garrett & Dunner, LLP

(57) ABSTRACT

Systems and methods for detecting the presence of a target nucleic acid in a sample via a recombinase polymerase amplification (RPA) reaction followed by a FEN1 cleavage detection reaction are disclosed. One aspect of the present disclosure relates to systems involving a sample collection device for collecting a sample and performing an RPA reaction on the sample, followed by the detection of the amplified product via a two-step FEN1 cleavage detection reaction which generates a fluorescent signal indicative of the presence of amplified product.

28 Claims, 23 Drawing Sheets

Specification includes a Sequence Listing.

(56)  References Cited

U.S. PATENT DOCUMENTS

| | | | | |
|---|---|---|---|---|
| 2008/0261208 | A1 | 10/2008 | Piepenburg et al. | |
| 2008/0293045 | A1* | 11/2008 | Piepenburg | C12Q 1/6844 |
| | | | | 435/6.12 |
| 2009/0017462 | A1 | 1/2009 | Piepenburg et al. | |
| 2009/0029421 | A1 | 1/2009 | Piepenburg et al. | |
| 2009/0253142 | A1* | 10/2009 | Allawi | C12Q 1/6827 |
| | | | | 435/6.1 |
| 2009/0269813 | A1 | 10/2009 | Piepenburg et al. | |
| 2009/0325165 | A1 | 12/2009 | Armes et al. | |
| 2010/0311127 | A1* | 12/2010 | Piepenburg | C12Q 1/6806 |
| | | | | 435/91.5 |
| 2011/0053153 | A1 | 3/2011 | Piepenburg et al. | |
| 2011/0053154 | A1 | 3/2011 | Piepenburg et al. | |
| 2011/0059506 | A1 | 3/2011 | Piepenburg et al. | |
| 2011/0065106 | A1 | 3/2011 | Armes et al. | |
| 2017/0065980 | A1* | 3/2017 | Nelson | B01L 7/52 |
| 2018/0021026 | A1* | 1/2018 | Nelson | A61B 10/02 |
| | | | | 422/507 |
| 2023/0313323 | A1* | 10/2023 | Roth | C12Q 1/6883 |
| | | | | 435/5 |

OTHER PUBLICATIONS

Olivier, M., "The Invader assay for SNP genotyping", *Mutat Res.*, Jun. 3, 2005, 573(1-2): 103-110 (9 pages).

Kersting, S. et al., "Multiplex isothermal solid-phase recombinase polymerase amplification for the specific and fast DNA-based detection of three bacterial pathogens", *Microchim Acta* (2014) 181:1715-1723.

Powell, M. L., et al., "New Fpg probe chemistry for direct detection of recombinase polymerase amplification on lateral flow strips", *Analytical Biochemistry*, 543 (2018) 108-115 (8 pages).

Li, J. et al., "Review: a comprehensive summary of a decade development of the recombinase polymerase amplification", *Analyst*, Jan. 2019, 144, 31 (38 pages).

* cited by examiner

A          # Reaction 1
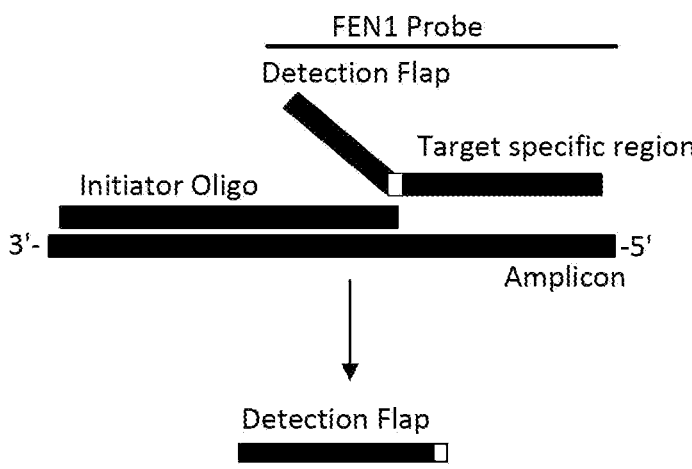
B          # Reaction 2
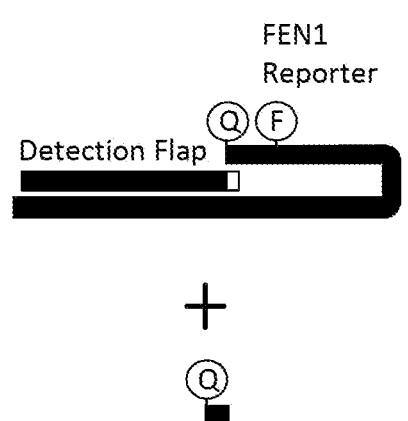
FIG. 1

Targeting the SARS-CoV-2 *RdRP* Gene

5'-TGA GTT ATG AGG ATC AAG ATG CAC TTT TCG CAT ATA CAA AAC GTA ATG TCA TCC CTA CTA

TAA CTC AAA TGA ATC TTA AGT ATG CCA TTA GTG CAA AGA ATA GAG CTC GCA CCG TAG CTG

GTG TCT CTA TCT GTA GTA CTA TGA CCA ATA GAC AGT TTC ATC AAA AAT TAT TGA AAT CAA

TAG CCG CCA CTA GAG GAG CTA CTG TAG TAA TTG GAA CAA GCA AAT TCT ATG GTG GTT GGC

ACA ACA TGT TAA AAA CTG TTT ATA GTG ATG TAG AAA ACC CTC ACC TTA TGG GTT GGG ATT

ATC CTA AAT GTG ATA GAG CCA TGC CTA ACA TGC TTA GAA TTA TGG CCT CAC TTG TTC TTG

CTC GCA AAC ATA CAA CGT GTT GTA GCT TGT CAC ACC GTT TCT ATA GAT TAG CTA ATG AGT

RdRP Forward Primer for RPA →      FEN1 Probe

GTG CTC AAG TAT TGA GTG AAA TGG TCA TGT GTG GCG GTT CAC TAT ATG TTA AAC CAG GTG

5' Detection Flap*

Initiator Oligo

GAA CCT CAT CAG GAG ATG CCA CAA CTG CTT ATG CTA ATA GTG TTT TTA ACA TTT GTC AAG

← RdRP Reverse Primer for RPA

CTG TCA CGG CCA ATG TTA ATG CAC TTT TAT CTA CTG ATG GTA ACA AAA TTG CCG ATA AGT

ATG TCC GCA ATT TAC AAC ACA GAC TTT ATG AGT GTC TCT ATA GAA ATA GA -3'

FEN1 detection oligos anneal to the reverse strand
RdRP Reverse Primer anneals to the reverse strand

FIG. 2

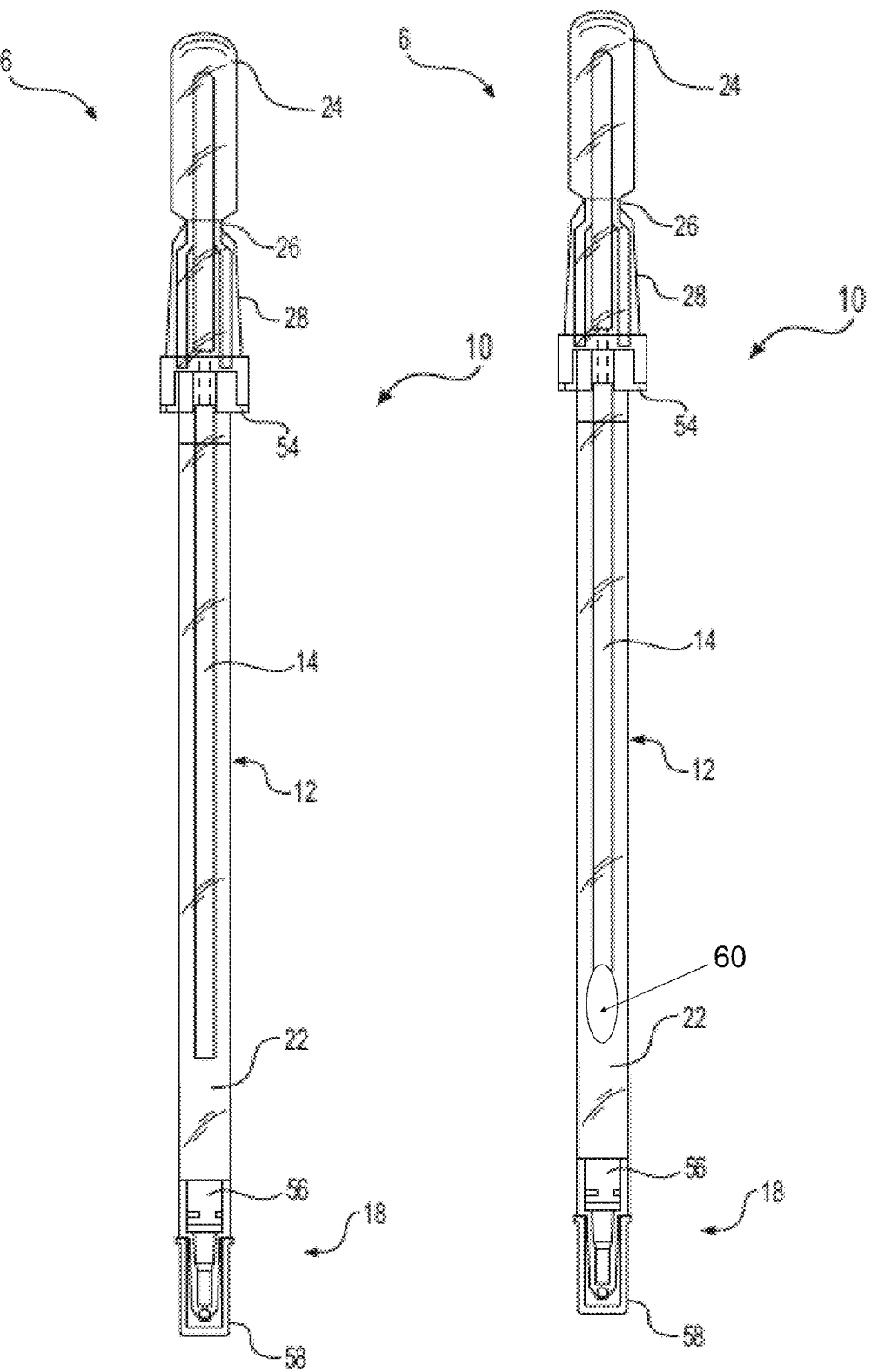
FIG. 8A                    FIG. 8B

Fen 1 detection after 5 minute RPA

FIG. 11

SARS-CoV-2 N gene

Internal Control

SEQUENCE LISTING

<160> NUMBER OF SEQ ID NOS: 25

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gacagcttga caaatgttaa aaacactatt agcata                                36

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tattgagtga aatggtcatg tgtggcggtt ca                                    32

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agcagttgtg gcatctcctg atgat                                            25

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
ctgggctcta cgaccggttc cacctggttt aacatatag                             39

<210> SEQ ID NO 5
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 5
agcgtgcagg tgcggagtag agccgcacct gcacgcggtc gtagagccca gaacga            56

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caacttcctc aaggaacaac attgccaaaa                                         30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tggagttgaa tttcttgaac tgttgcgact                                         30

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cgtgatgagg aacgagaaga ggcttgactg ccgccta                                 37

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
gttctgggct ctacgaccct gctcccttct gcgtag                                  36

<210> SEQ ID NO 10
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
agcgtgcagg tgcggagtag agccgcacct gcacgcggtc gtagagccca gaacga            56

<210> SEQ ID NO 11
<211> LENGTH: 160
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 11
```

```
caacuuccuc aaggaacaac auugccaaaa cgugcguagc gaauagugua gguggugcga      60
cggaauacga ugcgugagca cagcagagcg uaugggcaua aagugguggc acagugaaug     120
gcacugagcg agucgcaaca guucaagaaa uucaacucca                           160
```

```
<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
tcgatacagg gtccacgtta tgcccatacg ctctgc                               36
```

```
<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cgctcagtgc cattcactgt gccaccactt                                      30
```

```
<210> SEQ ID NO 14
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agcgtgcagg tgcggagtag agccgcacct gcacgccgtg gaccctgtat cgagca        56
```

```
<210> SEQ ID NO 15
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgattccgca atgcgagtcg aggcaaatgt taaaaacact attagcata               49
```

```
<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
accgcatcga atgcgagtcg agggtgaaat ggtcatgtgt ggcgg                    45
```

```
<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 17
ggccgtgaca gcttga                                                        16

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gctaatgagt gtgctcaagt                                                    20

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cgtgcgtagc gaatagtgta ggtggtgcga                                         30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cgctcagtgc cattcactgt gccaccactt                                         30

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tcgatacagg gtccacgtta tgcccatacg ctctgc                                  36

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tcgatacagg gtccacgtcg ctcagtgcca ttca                                    34

<210> SEQ ID NO 23
<211> LENGTH: 650
<212> TYPE: DNA
<213> ORGANISM: Severe acute respiratory syndrome coronavirus 2

<400> SEQUENCE: 23

-continued

```
tgagttatga ggatcaagat gcacttttcg catatacaaa acgtaatgtc atccctacta        60
taactcaaat gaatcttaag tatgccatta gtgcaaagaa tagagctcgc accgtagctg       120
gtgtctctat ctgtagtact atgaccaata gacagtttca tcaaaaatta ttgaaatcaa       180
tagccgccac tagaggagct actgtagtaa ttggaacaag caaattctat ggtggttggc       240
acaacatgtt aaaaactgtt tatagtgatg tagaaaaccc tcaccttatg ggttgggatt       300
atcctaaatg tgatagagcc atgcctaaca tgcttagaat tatggcctca cttgttcttg       360
ctcgcaaaca tacaacgtgt tgtagcttgt cacaccgttt ctatagatta gctaatgagt       420
gtgctcaagt attgagtgaa atggtcatgt gtggcggttc actatatgtt aaaccaggtg       480
gaacctcatc aggagatgcc acaactgctt atgctaatag tgtttttaac atttgtcaag       540
ctgtcacggc caatgttaat gcacttttat ctactgatgg taacaaaatt gccgataagt       600
atgtccgcaa tttacaacac agactttatg agtgtctcta tagaaataga                   650

<210> SEQ ID NO 24
<211> LENGTH: 129
<212> TYPE: RNA
<213> ORGANISM: Severe acute respiratory syndrome coronavirus 2

<400> SEQUENCE: 24
uacaacuucc ucaaggaaca acauugccaa aaggcuucua cgcagaaggg agcagaggcg        60
gcagucaagc cucuucucgu uccucaucac guagucgcaa caguucaaga aauucaacuc       120
caggcagca                                                               129

<210> SEQ ID NO 25
<211> LENGTH: 186
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 25
ccauaauacg acucacuaua gggagacaac uuccucaagg aacaacauug ccaaaacgug        60
cguagcgaau aguguaggug gugcgacgga auacgaugcg ugagcacagc agagcguaug       120
ggcauaaagu gguggcacag ugaauggcac ugagcgaguc gcaacaguuc aagaaauuca       180
acucca                                                                  186
```

DETECTION OF RECOMBINASE POLYMERASE AMPLIFICATION (RPA) AMPLICONS VIA FEN1 CLEAVAGE

REFERENCE TO SEQUENCE LISTING SUBMITTED ELECTRONICALLY

An official copy of the Sequence Listing is submitted electronically via EFS-WEB as an ASCII formatted sequence listing with a file named RPA-detection-SL.txt, created on Sep. 3, 2021, and having a size of 7,256 bytes. The sequence listing contained in this ASCII formatted document is part of the specification and is herein incorporated by reference in its entirety.

The present disclosure generally relates to systems, devices, compositions, and methods for analyzing a biological or medical sample from a subject or patient for the presence of a target nucleic acid. In some aspect, the systems, devices, compositions, and methods of the present disclosure may be used for diagnostic purposes. In other aspects, the systems, devices, compositions, and methods of the present disclosure may be used for surveillance testing purposes. Particularly, and without limitation, the present disclosure relates to a system or a method for analyzing or testing a sample for the presence of a target nucleic acid by performing a recombinase polymerase amplification (RPA) reaction followed by a FEN1 cleavage detection reaction.

The current gold standard for molecular detection of pathogens or biothreat agents is the polymerase chain reaction (PCR) amplification of a unique, conserved target sequence in combination with a hydrolysis probe that yields the release of one fluorophore per amplicon per cycle of the reaction. While specific and sensitive down to a single copy of target, due to the necessity of thermal cycling, PCR reactions commonly take over an hour to complete and confirm detection.

One aspect of the present disclosure uses an RPA reaction to amplify a nucleic acid target followed by a two-step FEN1 cleavage detection reaction to detect the amplified product. Another aspect of the present disclosure uses a combination of devices and molecular interactions that can begin amplification of a target immediately upon collection, for example via the use a sample collection device described in the present disclosure. In this aspect of the present disclosure a FEN1 cleavage detection reaction, particularly a two-step FEN1 cleavage detection reaction, is used to detect the RPA amplified product or amplicons. In some aspects of the present disclosure the FEN1 cleavage detection reaction is carried out in special reaction vessels described herein.

Recombinase polymerase amplification (RPA) allows for isothermal amplification of a region of interest. In some embodiments an RPA reaction may be performed at room temperature. This method of amplification, like PCR, is exponential and requires primers flanking the region of interest. However, addition of a collection of DNA-binding proteins combined with a strand-displacing polymerase eliminate the need for thermal cycling, allowing rapid amplification, even at room temperature.

Part of this process uses a recombinase which binds the oligonucleotide or primer and scans along the nucleic acid sequence template until it finds a homologous region at which it inserts the oligonucleotide or primer. This process is ATP-dependent and also requires Mg2+. To stabilize the D-loop where the recombinase inserts the primer into a double-stranded template, a single-stranded DNA binding (SSB) protein may be included in the reaction. Because the SSB protein competes with the recombinase for binding to the single-stranded primers another protein may be included to aid the loading of the recombinase onto the primer. These proteins work in concert to allow insertion of forward and reverse primers while a strand displacing polymerase extends these primers, leading to amplification. The strand-displacing polymerase is important to the isothermal nature of this reaction, as it prevents the need for thermo-mediated denaturation required in conventional PCR. This process continues on each newly created strand as well as all previous strands, making this amplification exponential.

Upon generation of a detectable amount of amplicon, two sequential FEN1 cleavage reactions, or a two-step FEN1 cleavage detection reaction, can be used to specifically detect the RPA generated amplicons or amplified product. This reaction depends on the highly specific 5' flap endonuclease activity of FEN1. This enzyme recognizes and cleaves off single-stranded 5' flaps hanging off of dsDNA, leaving nicks that can be ligated. This activity is used in the present disclosure to generate a method of amplicon detection through a two-step reaction mediated by FEN1: one on the amplified product or amplicon, and a second reaction fueled by the product of the first, which generates a fluorescent signal that can be detected (FIGS. 1A-1B).

In view of the above and other factors, the embodiments of the present disclosure have the potential to allow rapid amplification and detection of target nucleic acids in a sample via an RPA reaction followed by a two-step FEN1 cleavage detection reaction.

SUMMARY

The disclosed embodiments include methods for detecting the presence of a target nucleic acid in a sample. In some embodiments the methods include amplifying the target nucleic acid via a recombinase polymerase amplification (RPA) reaction thereby generating amplicons of the target nucleic acid. In preferred embodiments the RPA reaction comprises a forward primer and a reverse primer, wherein the forward and the reverse primer are single stranded. The disclosed methods further include detecting the generated amplicons via a FEN1 cleavage detection reaction, particularly a two-step FEN1 cleavage detection reaction, wherein the FEN1 cleavage detection reaction generates a fluorescent signal indicative of the presence of the target nucleic acid in the sample.

In some embodiments, an RPA reaction is used to amplify a nucleic acid target, wherein the amplified target is detected by the FEN1 cleavage detection reaction. In some embodiments a polymerase chain reaction (PCR) is used to amplify a nucleic acid target, wherein the amplified target is detected by the FEN1 cleavage detection reaction. In some embodiments a Strand Displacement Amplification (SDA) reaction is used to amplify a nucleic acid target, wherein the amplified target is detected by the FEN1 cleavage detection reaction.

According to other aspects of the invention, a system is described for detecting the presence of a target nucleic acid in a sample, the system including a device for collecting the sample and performing a recombinase polymerase amplification (RPA) reaction, the device comprising: (i) a tubular housing having a first end and a second end, (ii) a valved bulb reservoir detachably fitted to the first end of the tubular housing, (iii) a detachable end cap assembly at the second end of the tubular housing, and (iv) a tubular member comprising a longitudinal bore, a first end fluidically coupled to the valved bulb reservoir, and a second end configured for receiving the sample, wherein the tubular member contains RPA reagents deposited therein. In these embodiments, after the sample is received on the tubular member, the RPA reagents and the sample are brought in contact by the valved bulb reservoir releasing a buffer, thereby initiating the RPA reaction and generating RPA amplicons of the target nucleic acid. The systems of these embodiments may further comprise a vessel comprising reaction reagents for performing a FEN1 cleavage detection reaction using as template the RPA amplicons, wherein the FEN1 cleavage detection reaction generates a fluorescence signal indicative of the presence of the target nucleic acid in the sample.

According to other aspects of the invention, a method is described for detecting the presence of a target nucleic acid in a sample, the method comprising (a) providing a device comprising (i) a tubular housing having a first end and a second end, (ii) a valved bulb reservoir detachably fitted to the first end of the tubular housing, (iii) a cap assembly at the second end of the tubular housing, and (iv) a tubular member comprising a longitudinal bore, a first end fluidically coupled to the valved bulb reservoir, and a second end configured for receiving the sample, wherein the tubular member contains RPA reagents deposited therein; (b) removing the valved bulb reservoir and tubular member from the tubular housing; (c) collecting a sample at the second end of the tubular member; (d) replacing the valved bulb reservoir and tubular member into the tubular housing; (e) dispensing the contents of the valved bulb reservoir through the longitudinal bore of the tubular member causing the RPA reagents to come in contact with the sample and displace the RPA reagents and the sample into the tubular housing; (f) performing an RPA reaction within a region of the tubular housing proximal to the cap assembly thereby producing RPA amplicons; (g) providing a vessel comprising reaction reagents for performing a FEN1 cleavage detection reaction; (h) removing the cap assembly from the second end of the tubular housing of the device; (i) transferring the RPA amplicons from the tubular housing to the vessel; and (j) performing the FEN1 cleavage detection reaction, wherein the FEN1 cleavage detection reaction generates a fluorescence signal indicative of the presence of the target nucleic acid in the sample.

Embodiments according to the present disclosure solve many problems in the prior art. Exemplary embodiments discussed herein provide exceptional ease of use in a clinical or field setting. A minimally trained individual can collect and test a sample for the presence of a target nucleic acid. Exemplary embodiments of the present disclosure also provide for more rapid sample acquisition and testing.

Advantageously, embodiments according to the disclosure facilitate the ease and speed of sample acquisition, contributing to the comfort of the subject, the ability to collect a sample at the point-of-care, as well as decreasing the training level required of the health care worker taking the sample.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

FIG. 1A illustrates a first step of the two-step FEN1 cleavage detection reaction used for detection of a target nucleic acid in some embodiments of the present disclosure. FIG. 1B illustrates a second step of the two-step FEN1 cleavage detection reaction used for detection of a target nucleic acid.

FIG. 2 illustrates the design of and binding regions for RPA primers and FEN1 cleavage probes and oligos used for targeting of the SARS-CoV-2 RdRP gene for amplification and detection. FIG. 2 discloses SEQ ID NO: 23.

FIG. 8A-B are a side elevation views of two collection devices according to exemplary embodiments of the disclosure.

FIG. 11 illustrates the detection of RT-RPA amplicons by FEN1 cleavage when starting with different amounts of RNA copies of the RdRp gene, with the RPA reaction being carried out for about 5 min. Fluorescence was measured at every cycle, each cycle being 30 seconds long.

FIGS. 19A-B disclose SEQ ID NOS: 24-25, respectively, in order of appearance.

DETAILED DESCRIPTION

Figure 3A:
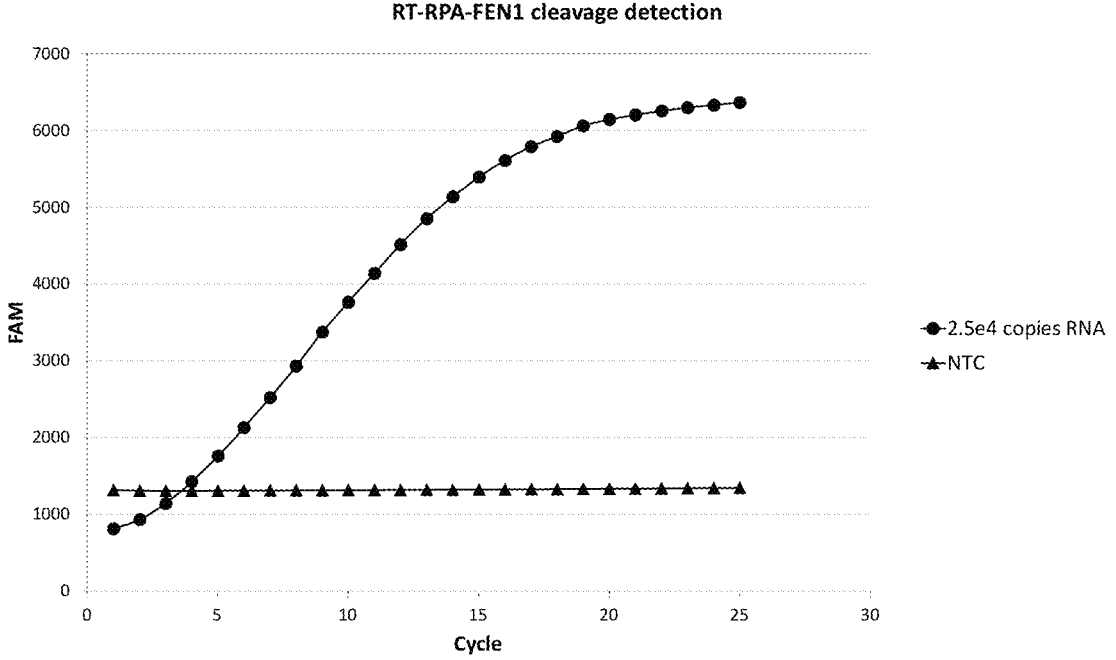
FIG. 3A-B illustrate the detection of RPA amplicons by FEN1 cleavage when starting with $2.5 \times 10^4$ copies of RNA molecules.

All references referred to in this disclosure are incorporated herein by reference in their entireties.

Units, prefixes and symbols may be denoted in their SI accepted form. Unless otherwise indicated, nucleic acids are written left to right in 5' to 3' orientation. Nucleotides may be referred to by their commonly accepted single-letter codes. Numeric ranges are inclusive of the numbers defining the range. The recitation of ranges of values herein is merely intended to serve as a shorthand method of referring individually to each separate value falling within the range. Unless otherwise indicated herein, each individual value is incorporated into the specification as if it were individually recited herein.

Unless specifically defined otherwise, all technical and scientific terms used herein have the same meaning as commonly understood by one of ordinary skill in the art to which this disclosure belongs. The materials, methods and examples are illustrative only and not limiting. The following is presented by way of illustration and is not intended to limit the scope of the disclosure.

As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

In some embodiments, the numerical parameters set forth in the specification (into which the claims are incorporated in their entirety) are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, numbers expressing quantities of ingredients, properties such as molecular weight, reaction conditions and results, and so forth, used to describe and claim certain embodiments of the present disclosure are to be understood as being modified in some instances by the term "about." One of ordinary skill in the art would understand the meaning of the term "about" in the context of the value that it qualifies. In some embodiments, the term "about" is used to indicate that a value includes the standard deviation of the mean for the device or method being employed to determine the value.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition that "comprises," "has" or "includes" one or more features is not limited to possessing only those one or more features and can cover other unlisted features. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element as essential to the practice of the present disclosure.

The term "consisting essentially of" allows for the presence of additional materials or steps that "do not materially affect the basic and novel characteristic(s)" of the claimed invention.

The term "consisting of" refers to compositions, methods, and respective components thereof as described herein, which are exclusive of any element not recited in that description of the embodiment.

The terms "disease" or "disorder" are used interchangeably herein, and refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, sickness, illness, complaint, indisposition, or affection.

As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

As used herein, the term "nucleic acid," in its broadest sense, includes any compound and/or substance that comprises a polymer of nucleotides linked via a phosphodiester bond. These polymers are often referred to as oligonucleotides or polynucleotides, depending on the size. The terms "polynucleotide sequence" and "nucleotide sequence" are also used interchangeably herein.

The term "subject" refers to an animal, for example a human. The term "patient" is used interchangeably herein.

Without being limited by examples, a biological or medical sample, as referred to in the present disclosure, may include cells, tissues, blood, blood plasma, saliva, nasal discharge, mucus, semen, urine, amniotic fluid, tears, lymph, vaginal lubrication, aqueous humour, phlegm, earwax, breast milk, or any other type of body fluid from a subject or patient. In some embodiments, the biological or medical sample may be taken directly from a subject or a patient. In some embodiments, the biological or medical sample may be taken from a surface where the sample has been deposited by the subject or patient.

It should be understood that this disclosure is not limited to the particular methodology, protocols, and reagents, etc., described herein and as such can vary. The terminology used herein is for the purpose of describing particular embodiments only, and is not intended to limit the scope of the present disclosure, which is defined solely by the claims.

The present disclosure generally relates to systems, devices, compositions, and methods for analyzing or testing a biological or medical sample from a subject or patient for the presence of a target nucleic acid. More particularly, and without limitation, the present disclosure relates to a method for analyzing a sample by performing a recombinase polymerase amplification (RPA) reaction followed by a FEN1 cleavage detection reaction to detect the amplicons generated by RPA, which would indicate the presence of the target nucleic acid in the sample. In some embodiments the presence of the target nucleic acid in the sample correlates with the presence of a disease. Particularly, in some embodiments the methods may include surveillance testing of subjects to determine if a subject's sample is positive for the presence of a target nucleic acid. In other embodiments the methods may further include diagnosing a subject with a disease based on the indication of the presence of a target nucleic acid in the sample from the subject. In some embodiments, the methods further comprise amplifying and detecting an internal control sequence. In some embodiments the methods further comprise comparing the detected internal control sequence with the detected target nucleic acid sequence.

Surveillance testing comprises taking a sample from a subject to determine the presence or absence of a target nucleic acid in the sample. Surveillance testing may be carried out for various purposes, such as for example, to detect the presence of a virus in a sample from a subject. Surveillance testing for purposes like this may be carried out under various circumstances. For instance, surveillance testing may be carried out at airports, stores of any kind including grocery stores, emergency rooms, hospitals, and any other place prior to admission of the subject on the premises. For instance, during a pandemic, surveillance testing may be carried out at the entrance of a store, wherein a sample from a customer may be taken to determine if the sample is positive or negative for the presence of a target nucleic acid from a virus. In another scenario, surveillance testing may be carried out at an airport checkpoint to determine if a sample from a passenger is positive or negative for the presence of a target nucleic acid of a virus. Such surveillance testing provides the means to stop or reduce the transmission of a virus, for instance.

In some embodiments the disease is a coronavirus disease. In some embodiments the disease is COVID-19. In some embodiments the target nucleic acid comes from SARS-CoV-2. In some embodiments the target nucleic acid is the RdRp gene of SARS-CoV-2. In some embodiments the target nucleic acid is the N gene of SARS-CoV-2.

In some embodiments the disease is Influenza A. In some embodiments the disease is Influenza B. In some embodiments the target nucleic acid comes from a virus. In some embodiments the virus is an influenza virus. In some embodiments, the virus is a coronavirus. In some embodiments, the target nucleic acid comes from bacteria.

Some embodiments of the present disclosure comprise devices for rapid collection and testing of a sample from a subject. In some embodiments, samples can be collected at the point-of-care for analysis by personnel, even personnel having very little training. Conventional methods require collecting a sample from a subject or patient, transferring the sample to a reservoir, and then processing the sample prior to testing, which often occurs at a second location. According to one aspect of the disclosure, rapid and simple collection and testing of a sample for the presence of a target nucleic acid is provided, without the need for transferring the sample to another reservoir, for processing the sample prior to the running a test, or for having to transport the sample to a second location for testing.

In some embodiments the amplification of the target nucleic acid via RPA, SDA, or PCR (or any other method of nucleic acid amplification used in the present invention) is immediately followed by a detection of the amplified target via a FEN1 cleavage detection reaction. In other embodiments the amplification of the target nucleic acid via RPA, SDA, or PCR (or any other method of nucleic acid amplification used in the present invention) is not immediately followed by a detection of the amplified target via a FEN1 cleavage detection reaction. For instance, in some embodiments, the nucleic acid amplification step (e.g., RPA, SDA, or PCR) may be run and then the reaction may be stored at room temperature or 4° C. for a period of time, even overnight or longer, before detection by a FEN1 cleavage detection reaction. In some embodiments the RPA, SDA, or PCR reaction may be run and then stored at any temperature that allows preservation of the nucleic acids for later detection. In some embodiments, the RPA, SDA, or PCR reaction may be run and then stored at about −80° C., −20° C., or 4° C. before nucleic acid detection. In some embodiments, the RPA, SDA, or PCR reaction may be run and then stored for a period of time at any suitable temperature that allows preservation of the nucleic acids, including room temperature, before nucleic acid detection. For example, in some embodiments, the RPA, SDA, or PCR reaction may be run and then stored at a suitable temperature that allows preservation of the nucleic acids for less than an hour, one or more hours, 1 day, 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 1 year, or more than one year before nucleic acid detection.

Without being limited by examples, sample collection devices used to in the methods described herein may, for example, include the collection devices of US 2018/0021026 A1, incorporated herein by reference in its entirety. For instance, FIG. 8A-B provide illustrative and alternative embodiments of a sample collection device 10. The sample collection device 10 may have an elongated tubular housing 12 into which a tubular member 14 or the like may be received. A valved bulb reservoir 16, which is connected to the tubular member 14, is removably mounted at one end of tubular housing 12. In an illustrative embodiment, valved bulb reservoir 16 may contain one or more fluids or reagents which can be dispensed and mixed with a sample collected in tubular member 14. In some embodiments tubular member 14 is a capillary (FIG. 8A). In alternative embodiments tubular member 14 comprises a longitudinal bore, with a first end fluidically coupled to the valved bulb reservoir, and a second end connected or in contact with a swab, a swab section or a swab material 60 for receiving a sample (FIG. 8B). In some embodiments the one or more fluids or reagents are one or more buffers. An end cap assembly 18 may be mounted at an opposite end of tubular housing 12 and may include a dispensing spout 56 and a removable cover or cap 58. Dispensing spout 56 can optionally include one or more filters. A sample is obtained by a user by placing capillary tip 20 (FIG. 8A) proximate to a sample to be analyzed to draw it into the capillary, or by receiving the sample on the swab at the end of tubular member 14 (FIG. 8B). Sample collection device 10 advantageously permits quick and easy sample collection with tubular member 14 removed from tubular housing 12, followed by dispensation of an analytical fluid, for example a buffer solution, from valved bulb reservoir 16 through the longitudinal bore of tubular member 14, to expel the sample and the analytical fluid into the tubular housing 12, particularly, chamber 22. Thereafter, the sample mixed with any analytic fluid can be dispensed from tubular housing 12, for example via spout 56 in an illustrative embodiment, for downstream analysis.

In some embodiments, the sample collection device may further comprise an adapter for fluidically coupling the tubular member to the valved bulb reservoir. In some embodiments wherein the tubular member comprises a capillary, the sample collection device may further comprise an adapter fluidically coupling the capillary to the valved bulb reservoir, wherein the adapter comprises a vent for allowing air in a bore of the capillary to be displaced. In some embodiments the end cap assembly comprises a luer lock tip. In some embodiments the sample collection device further comprises a frangible seal in the valved bulb reservoir for fluidically isolating the valved bulb reservoir from the tubular member, wherein the frangible seal is rupturable by manipulation. Although illustrative embodiments of the disclosure use a valved bulb reservoir, other types of valves and reservoirs are possible, such as check valve, an umbrella valve, or an ePTFE vent.

In some embodiments the RPA reaction for amplifying a target nucleic acid in a sample may be carried out within the sample collection device. In some embodiments when the RPA reaction is carried out within the sample collection device the RPA reaction reagents or components may be dried down in the swab of an exemplary sample collection device. In this case, after the sample has been collected on the swab, the valved bulb reservoir may be altered to release a buffer, e.g., a rehydration buffer, through the longitudinal bore of the tubular member, bringing the RPA reaction reagents immediately in contact with the sample collected on the swab (FIG. 8B). In other embodiments the RPA reaction reagents may be dried down within the tubular housing 12, for example in chamber 22 of the tubular housing. In some embodiments the rehydration buffer may contain Mg2+, an essential cofactor for the DNA-binding enzymes in the RPA reaction, so that the reaction is initiated only when it has been appropriately rehydrated and brought in contact with the collected sample.

In some embodiments, to prevent the RPA reaction from running indefinitely, ATP, which is necessary for the recombinase activity, may be limited. Alternatively, in some embodiments another chamber of buffer can be integrated into the device and the reaction can be diluted upon completion, effectively preventing further amplification.

In some embodiments, upon rehydration, amplification of the selected region of the target RNA or DNA will begin immediately at room temperature. In some embodiments the dried down RPA reaction reagents or components may include target-specific oligonucleotides or oligos for amplification. In some embodiments, the dried down reaction components may also include a reverse transcriptase enzyme and reverse transcription reagents to allow for essentially simultaneous conversion of RNA to cDNA, increasing the stability of certain samples (for example, those containing viral RNA) in order to prevent degradation before detection.

In some embodiments the RPA reaction is not carried out within the sample collection device. In some embodiments the RPA reaction is carried out in a tube, a well, or any other type of vessel appropriate for this type of reaction. In some embodiments the RPA reaction reagents or components may be dried down within the vessel. In some embodiments the dried down RPA reaction reagents or components may include target-specific oligonucleotides for amplification.

In some embodiments the RPA reaction components or reagents comprise a recombinase. In some embodiments the RPA reaction components or reagents comprise a uvsX recombinase. In some embodiments the uvX recombinase is from a T4 bacteriophage but other homologous recombinases from other organisms may be also be suitable for the methods of the present disclosure. In some embodiments the recombinase is bacterial RecA, archaeal RadA, or Rad51 from eukaryotes. In order to stabilize the D-loop where the recombinase inserts the primer into the double-stranded template, a single-stranded DNA binding protein may be included in the RPA reaction. In some embodiments the single-stranded DNA binding protein is T4 bacteriophage gp32. In some embodiments the single-stranded DNA binding protein is bacterial single-strand binding protein (SSB), or eukaryotic replication protein A. Because the SSB protein competes with the recombinase for binding to the single-stranded primers another protein may be included to aid the loading of the recombinase onto the primer. In some embodiments the loading protein is uvsY. In some embodiments the loading protein is RecOR or Rad52. In some embodiments magnesium acetate may be added to start the RPA reaction. In some embodiments at least one forward primer or oligonucleotide and at least one reverse primer or oligonucleotide are included in the RPA reaction for amplifying a target nucleic acid. In preferred embodiments the primers or oligonucleotides used in the RPA reaction are single stranded. In some embodiments a forward primer and a reverse primer are included in the RPA reaction at the same concentration each. In some embodiments a forward primer and a reverse primer are included in the RPA reaction at different concentrations. Particularly, in some embodiments, making the RPA reaction asymmetric by adding more of one primer than the other may enhance consistency of amplification. In some embodiments, for example, one primer is added at 1 µM and the other primer is added at 480 nM within the RPA reaction. The RPA reaction includes deoxynucleotides (dNTPs) for amplifying the target nucleic acid. In preferred embodiments the dNTPs are not chain-terminating dNTPs. In preferred embodiments the dNTPs are not labeled with any markers.

The RPA proteins work in concert to allow insertion of forward and reverse primers while a strand displacing polymerase extends these primers, leading to amplification. In some embodiments the strand displacing polymerase which extends the primers is DNA polymerase I. In some embodiments the polymerase is the Klenow fragment or the large fragment of *E. coli* DNA polymerase I. In some embodiments the polymerase is Bsu polymerase. In some embodiments the polymerase is Bst polymerase. In some embodiments the polymerase is a variation of Bst polymerase. In some embodiments the polymerase has a high activity at about 30° C. to about 42° C. In some embodiments the polymerase has a high activity at about 37° C. to about 42° C. In some embodiments the polymerase lacks 5' to 3' exonuclease activity. In some embodiments the polymerase lacks 5' to 3' exonuclease activity and possesses activity at about 30° C. to about 42° C. The strand-displacing polymerase used may control the isothermal nature of this reaction, as it may prevent the need for a thermo-mediated denaturation required in conventional PCR cycling. This amplification process continues on each newly created strand as well as all previous strands, making this amplification exponential. In some embodiments, after the RPA reaction is completed, the RPA reaction components or reagents may be deactivated. In some embodiments the recombinase is temperature-sensitive and its activity is terminated at a non-permissive temperature. In some examples a recombinase has a permissive temperature of 42° C. or below. In some embodiments the non-permissive temperature of a recombinase is above 42° C. In some embodiments the activity of the recombinase is not restored after it has been terminated at the non-permissive temperature.

Furthermore, in some embodiments, reverse transcriptase reagents or components are included in the RPA reaction so that RNA can be converted to complementary DNA (cDNA) simultaneously with amplification by RPA. In some embodiments a reverse transcription (RT) reaction is carried out separately than the RPA reaction. In some embodiments the reverse transcriptase used is M-MLV reverse transcriptase. In some embodiments the RT reaction includes 200 units of M-MLV reverse transcriptase. In some embodiments the RT reaction includes 40 units of M-MLV reverse transcriptase.

In some embodiments the RPA reaction takes about 20 minutes or less to generate a detectable amount of amplicon.

In some embodiments the RPA reaction takes about 10 minutes or less to generate a detectable amount of amplicon. In some embodiments the RPA reaction takes about 5 minutes or less, about 4 minutes or less, about 3 minutes or less, about 2 minutes or less, about 90 seconds or less, or about 1 minute or less to generate a detectable amount of amplicon. In some embodiments the RPA reaction is carried out at room temperature. In some embodiments the RPA reaction is carried out at any temperature within the range of about 30-42° C. Because the recombinase activity is ATP-dependent, an ATP regeneration system comprised of phosphocreatine and creatinine kinase may also be included in some embodiments of the present disclosure. In some embodiments removing this system and limiting the amount of ATP may be a way to preset this reaction to run for a specific amount of time, thereby preventing excess unwanted, nonspecific product formation. In some embodiments careful regulation of the Mg2+ concentration, a cofactor which may be essential in the reaction, can also provide control of the RPA reaction.

Upon generation of amplicons by the RPA reaction, two sequential FEN1 cleavage reactions (a two-part FEN1 cleavage detection reaction) can be used to specifically detect the amplified target sequence or amplicons. These reactions depend on the highly specific 5' flap endonuclease activity of FEN1. In some embodiments this FEN1 enzyme is a thermostable FEN1 enzyme. In preferred embodiments this FEN1 enzyme is a thermostable FEN1 enzyme. This enzyme recognizes and cleaves off single-stranded 5' flaps hanging off of dsDNA, leaving nicks that can be ligated. This activity can be used to generate a method of amplicon detection through two distinct reactions mediated by FEN1: one on the amplified target sequence or amplicon, and a second reaction fueled by the product of the first, which generates a fluorescent signal that can be detected (FIGS. 1A-1B). Reaction 1 of FIG. 1A consists of two unique oligonucleotides, an initiator oligonucleotide and a FEN1 probe oligonucleotide. This reaction takes place on the amplicon. The initiator oligonucleotide binds upstream of the FEN1 probe oligonucleotide with at least one base pair mismatch at the 3' end (e.g., a single base pair mismatch), where it overlaps with the target specific region of the FEN1 probe oligonucleotide. The FEN1 probe oligonucleotide also contains a 5' detection flap that is not complementary to the amplicon. These two oligonucleotides create a 5' flap structure recognized by FEN1 that leads to cleavage of the 5' flap from the FEN1 probe oligonucleotide. While the single base mismatch at the end of the initiator oligonucleotide enhances FEN1 efficiency, in some embodiments the initiator oligonucleotide is completely complementary to the amplicon (e.g., no base pair mismatch). However, it is essential that there be a physical overlap, e.g., a single base overlap, between the initiator oligonucleotide and the target specific region of the FEN1 probe oligonucleotide so that FEN1 may recognize the structure created by the two oligonucleotides and cleave off the detection flap at the correct base.

The robust detection in RPA and SDA reactions generated by FEN1 was unexpected given scientific documentation that components of the RPA and SDA reactions could inhibit FEN1 detection. For example, the uvsX and uvsY proteins in the RPA reaction were expected to easily alter the precise oligonucleotide binding temperatures that are necessary for the FEN1 reaction. The uvsX and uvsY proteins could further sterically hinder FEN1, blocking its binding to the necessary oligos and preventing detection. Furthermore, for both RPA and SDA, the strand displacing polymerases present in both of these reactions that are essential to their function are capable of extending oligonucleotides necessary for and generated by the FEN1 reaction. Extension of the initiator oligo or flap oligo by even a single base could inhibit signal generation due to the precision of the FEN1 detection reaction. FEN1 reaction components would additionally be expected to inhibit isothermal amplification reactions. Both RPA and SDA use strand displacing polymerases to displace the previously generated strand and continue exponential amplification without the need to for a 95° C. denaturation step. This strand displacing polymerase generates a structure that can be recognized and cleaved by a 5' flap endonuclease like FEN1. This would be expected to lead to cleavage of each strand as it is being displaced, preventing exponential amplification in the presence of FEN1. Furthermore, the oligos necessary for the detection of FEN1 would be expected to be inhibitory to RPA. Extension of either the flap probe or initiation oligo would remove the binding site for the primer on the same strand, greatly inhibiting further amplification. Nevertheless, in exemplary embodiments of the present disclosure, robust results were obtained in RPA or SDA reactions followed by FEN1 cleavage detection.

This cleaved detection flap feeds the second FEN1 cleavage reaction, which includes a FEN1 reporter oligonucleotide comprising a hairpin structure with a quencher or fluorophore on the 5' end, with an adjacent complementary quencher or fluorophore (Reaction 2 of FIG. 1B). The cleaved detection flap binds to the single stranded portion of the FEN1 reporter oligonucleotide, where the cleaved detection flap will physically overlap, for example, by a single base, with the double stranded region of the FEN1 reporter hairpin. This provides a structure that can be recognized by the FEN1 endonuclease, allowing the 5' fluorophore or quencher to be cleaved off, unquenching the fluorophore that can now be detected by optical instrumentation, such as for example, a real-time PCR detection instrument. In some embodiments the first and second steps of the FEN1 cleavage detection reaction occur simultaneously or within a same vessel, same tube, same well, or same reaction chamber, so that the cleaved flap generated in the first step of the first reaction is continuously being fed into the second step of the reaction.

In some embodiments of the disclosure after the RPA reaction has been completed, the RPA reaction, or an aliquot thereof, containing the generated amplicons, is added directly to a vessel containing reagents for performing the FEN1 cleavage detection reaction. In other embodiments the completed RPA reaction, or an aliquot thereof, is first diluted before being added to a vessel containing reagents for perming the FEN1 cleavage detection reaction. In some embodiments the FEN1 cleavage detection reaction reagents or components are added together or separately to the completed RPA reaction or an aliquot thereof.

In some embodiments, following RPA amplification in a sample collection device of the present disclosure, the reaction can be transferred, for example, drop-wise into a reaction vessel for carrying out the FEN1 cleavage detection reaction. To prevent amplicon contamination, a Luer lock tip or other connection that prevents accidental spills of RPA product may be used to transfer the RPA reaction product from the sample collection device to the reaction vessel for the FEN1 cleavage detection detection.

In some embodiments the FEN1 cleavage detection reaction requires a denaturation step. The denaturation step allows for the separation of the strands of the double stranded amplicons and the annealing of FEN1 detection oligos to the amplicons. In some embodiments the denaturation step deactivates RPA proteins. In some embodiments the RPA reaction or aliquot thereof, containing the generated amplicons, may undergo a denaturation step followed by the FEN1 cleavage detection reaction. In some embodiments the FEN1 enzyme is a thermostable enzyme. In preferred embodiments the FEN1 enzyme is a thermostable enzyme. In some embodiments this denaturation step comprises heating the RPA reaction or an aliquot thereof to about 95° C. or above. In some embodiments the denaturation step is carried out for about 100-300 seconds. In some embodiments the denaturation step is carried out for about 5 min or less, for about 2.5 minutes or less, for about 1 minute or less, for about 30 seconds or less, or for about 10 seconds or less. In some embodiments the denaturation step is carried out before the RPA amplicons are put in contact with the FEN1 cleavage detection reaction components or reagents. In some embodiments the denaturing step is carried out after the RPA reaction amplicons or an aliquot thereof is put in contact with the FEN1 cleavage detection reaction components or reagents. For example, in some embodiments the RPA reaction amplicons or an aliquot thereof, containing the generated amplicons, is mixed with the FEN1 cleavage detection reaction components or reagents and the reaction temperature is brought to a high temperature for the denaturation step, before the temperature is decreased or dropped for generation of fluorescence and detection via the FEN1 cleavage detection reaction.

In some embodiments, essential to carrying out the FEN1 cleavage detection reaction as a mode of detection is that the melting temperature of the target specific region of the FEN1 probe oligonucleotide and the detection flap be near each other, for example between about 60° C. and about 70° C., and that the reaction be run at the same temperature as both melting temperatures. At their Tm's, the probe and detection flap are in equilibrium between bound and unbound, allowing FEN1 to generate constant product. This allows generation of multiple flaps per amplicon and multiple fluorophores per detection flap, which ultimately yields to exponential signal generation and greatly enhanced sensitivity. Thus, in some embodiments after a denaturation step at, for example 95° C., the FEN1 cleavage detection reaction proceeds at an isothermal detection step held at the Tm of the associated FEN1 probe target specific region and detection flap The FEN1 cleavage detection reaction may be carried out in any type of reaction vessel appropriate for signal detection, such as for example, fluorescence signal detection. In some embodiments the components or reagents used for the FEN1 cleavage detection reaction may be easily dried in the bottom of a reaction vessel.

Figure 9:
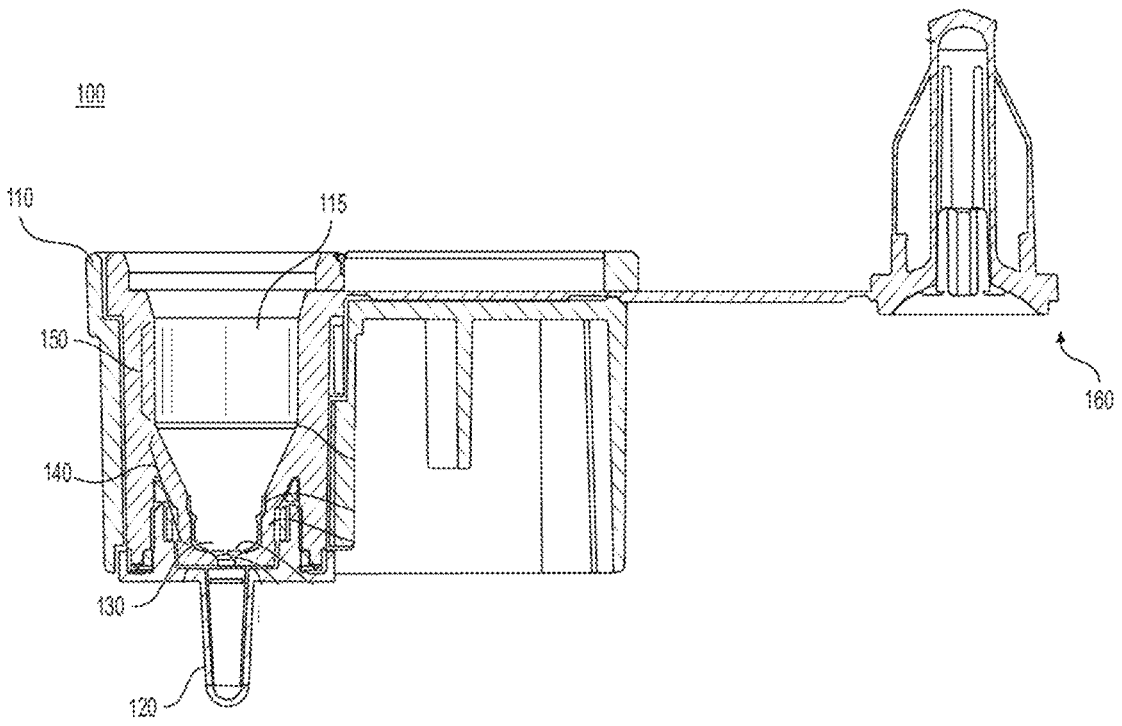
FIG. 9 is a side view of an exemplary reaction vessel for performing a FEN1 cleavage detection reaction according to exemplary embodiments of the disclosure.

In some embodiments the FEN1 cleavage detection reaction may be carried out in a vessel like the self-metering reaction device of US 2017/0065980 A1, incorporated herein by reference in its entirety. FIG. 9 illustrates a reaction vessel capable of self-metering the correct amount of fluid needed for a reaction, such that the fluid that is dispensed into the reaction vessel does not need to be a pre-metered amount. FIG. 9 illustrates a self-metering reaction device 100 comprising a cartridge 110, which houses a device chamber 115, reaction chamber 120, a metering reservoir 130, a sample reservoir 140, an overflow chamber 150, and a plunger 160. Metering reservoir 130 may be configured to hold a specific amount of fluid to be discharged into reaction chamber 120 as one of the reactants of the reaction. More specifically, metering reservoir 130 may be configured to hold a specific amount of fluid when plunger 160 becomes engaged and creates a seal with metering reservoir 130. Reaction chamber 120 may be configured to hold components or reagents for a reaction, such as for example FEN1 cleavage detection reaction components or reagents. In some embodiments, the FEN1 cleavage detection reaction components or reagents are dried down at the bottom of reaction chamber 120.

In some embodiments, the RPA reaction and the FEN1 cleavage detection reaction are carried out within the same vessel or tube. In some embodiments the sample is mixed with the RPA reaction reagents and FEN1 cleavage detection reaction reagents within the same vessel or tube for amplification and detection to occur in the same tube or vessel, without having to separate the reactions. In some embodiments, the sample is mixed with reverse transcription (RT) reagents, RPA reaction reagents, and FEN1 cleavage detection reaction reagents within the same vessel or tube for reverse transcription, amplification, and detection to occur in the same tube or vessel, without having to separate the reactions. Carrying out the RPA and FEN1 reactions, or the RT, RPA and FEN1 reactions within the same vessel or tube can greatly reduce the time for sample processing, and target amplification and detection.

In some embodiments, in order to carry out the RPA and FEN1 reactions, or the RT, RPA and FEN1 reactions within the same vessel or tube, the FEN1 probe oligonucleotide is blocked with a C3 spacer to prevent the FEN1 probe oligonucleotide from acting as a primer during the RPA reaction. In some embodiments, the 3' end of the FEN1 probe oligonucleotide is blocked with the C3 spacer. In some embodiments, phosphorylation or an inverted dT at the 3' of the FEN1 probe oligonucleotide may be used to prevent the FEN1 probe oligonucleotide from acting as a primer during the RPA reaction. In some embodiments, the sensitivity of the FEN1 probe oligonucleotide may be enhanced by creating mismatches at the 3' end or throughout the FEN1 probe oligonucleotides. In some embodiments, the sensitivity of the FEN1 probe oligonucleotide may be enhanced by incorporating peptide nucleic acids (locked nucleic acids).

In some embodiments, in order to carry out the RPA and FEN1 reactions, or the RT, RPA and FEN1 reactions within the same vessel or tube, one of the RPA primers is used as the initiator oligonucleotide of the FEN1 cleavage detection reaction. Using an RPA primer as part of the FEN1 cleavage detection reaction eliminates the need to add an additional initiator oligonucleotide which could potentially act as an undesired primer during the RPA reaction.

In some embodiments, in order to carry out the RPA and FEN1 reactions, or the RT, RPA and FEN1 reactions within the same vessel or tube, the FEN1 probe oligonucleotide is blocked from acting as a primer during the RPA reaction, and one of the RPA primers is used as the initiator oligonucleotide of the FEN1 cleavage detection reaction. In some embodiments, in order to carry out the RPA and FEN1 reactions, or the RT, RPA and FEN1 reactions within the same vessel or tube, the sensitivity of the FEN1 probe oligonucleotide is enhanced, and one of the RPA primers is used as the initiator oligonucleotide of the FEN1 cleavage detection reaction.

EXAMPLES

Example 1

Methods

RPA reaction: 25 μL RPA reactions were set up by mixing RPA proteins (a recombinase, a recombinase loading protein, a DNA binding protein), a polymerase, a forward and a reverse primer at a final concentration of 480 nM each, 2.5 μL of sample to be tested, and Magnesium acetate at a final concentration of 14 mM. However, in some experiments, it was found that making the assay asymmetric by adding more of one primer than the other (e.g. 1 uM of the reverse primer and 480 nM of the forward primer) enhanced consistency of the amplification. The reaction started immediately even at room temperature but the tubes containing the RPA reaction mix were placed in a PCR machine and heated to about 30-42° C. for up to 20 minutes as quickly as possible following the addition of magnesium. In some assays, when the starting material was RNA, reverse transcription (RT) reaction reagents, including a reverse transcriptase, were added to the RPA reaction mix so that the RNA could be converted to cDNA before amplification by RPA.

FEN1 Detection Reaction: 25 μL reactions were set up by mixing 22.5 μL of a mixture of FEN1 detection reagents with 2.5 μL of the resulting RPA reaction, but the reaction can also be set up by adding the individual FEN1 detection reagents directly to the RPA reaction sample. The final concentrations of the FEN1 detection reagents in the 25 μL reaction were as follows: Tris (pH 8.4) at 20 mM, KCl at 50 mM, Magnesium acetate at 5 mM, nCoV initiator oligonucleotide at 200 nM, nCoV FEN1 probe oligonucleotide at 1 uM, FEN1 reporter oligonucleotide at 200 nM, and thermostable FEN1 at a concentration of at least 96 units/25 μL reaction (3.84 U/μL). A higher concentration of thermostable FEN1 can also be used; for example, up to a concentration of 200 units of thermostable FEN1 per reaction. Generally, 32 units of thermostable FEN1 per reaction can allow for effective detection. 10% Glycerol may also be present in the reaction. Once the FEN1 reaction was set, the reaction vessel was heated to about 95° C. for about 100-300 seconds (denaturation step), unless otherwise specified, and then cooled to about 58-70° C. (e.g., about 63° C.) for the generation and detection of the fluorescence.

Targeting the SARS-CoV-2 RdRP Gene (RdRp Assay)

The SARS-CoV-2 RdRP gene was used as the target for this assay, to test the detection of RPA amplicons via a FEN1 cleavage detection reaction. FIG. 2 illustrates, within the reverse transcribed gene, the region corresponding to the RdRP Forward Primer, and the regions where the RdRP Reverse Primer, the FEN1 probe oligonucleotide, and the initiator oligonucleotide would anneal on the reverse strand.

Figure 3B:
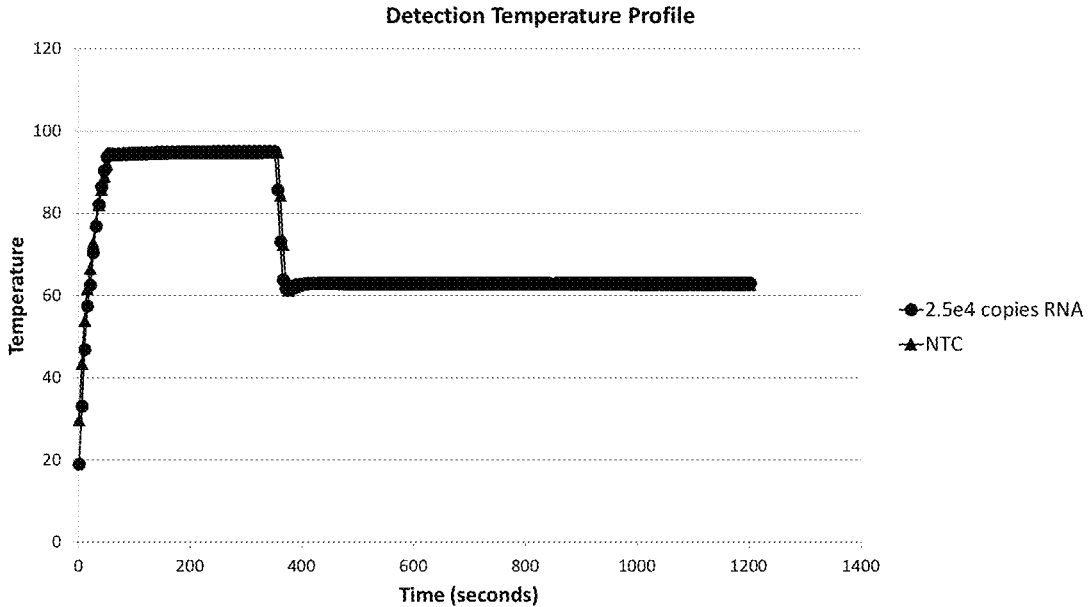

$2.5 \times 10^4$ copies of RNA molecules generated in vitro from the SARS-CoV-2 RdRP gene were used to set up an RT-RPA reaction followed by a FEN1 cleavage detection reaction as described in the methods section above, with the RPA reaction being carried out for 20 minutes. As illustrated in FIG. 3A, the amplification is promptly detected soon after about 4 cycles (each cycle is about 30 seconds) in the experimental sample in comparison to the water control (NTC). The control used can also be TE buffer, universal transport media, saliva, saline, etc. FIG. 3B maps out the denaturation step and the FEN1 cleavage detection reaction as functions of temperature and time.

Figure 4A:
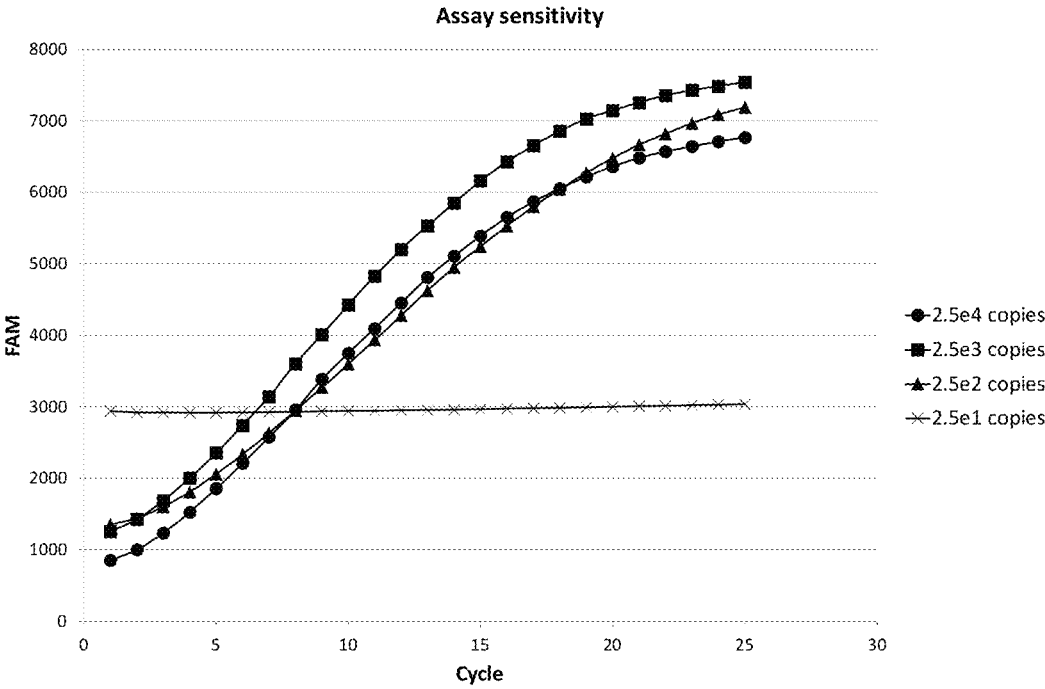
FIG. 4A-B illustrate the detection of RPA amplicons by FEN1 cleavage when starting with different amounts of RNA molecules, with the RPA reaction being carried out for about 20 min.
Figure 4B:
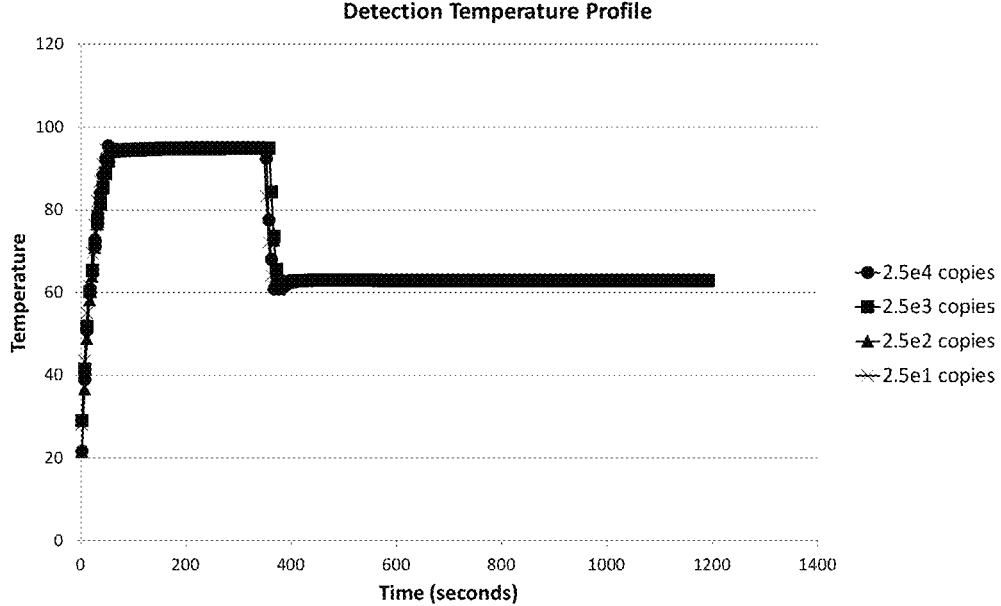

In order to demonstrate the sensitivity of the assay, RT-RPA reactions were set up using different amounts of RNA copies of the RdRP gene followed by FEN1 cleavage detection as described in the methods section above, with the RPA reaction being carried out for 20 minutes. As FIG. 4A illustrates, the nucleic acid amplification is promptly detected even using a lower amount of RNA ($2.5 \times 10^2$ RNA copies of the RdRP gene). FIG. 4B maps out the denaturation step and the FEN1 cleavage detection reaction for each of the samples as functions of temperature and time.

Figure 5A:
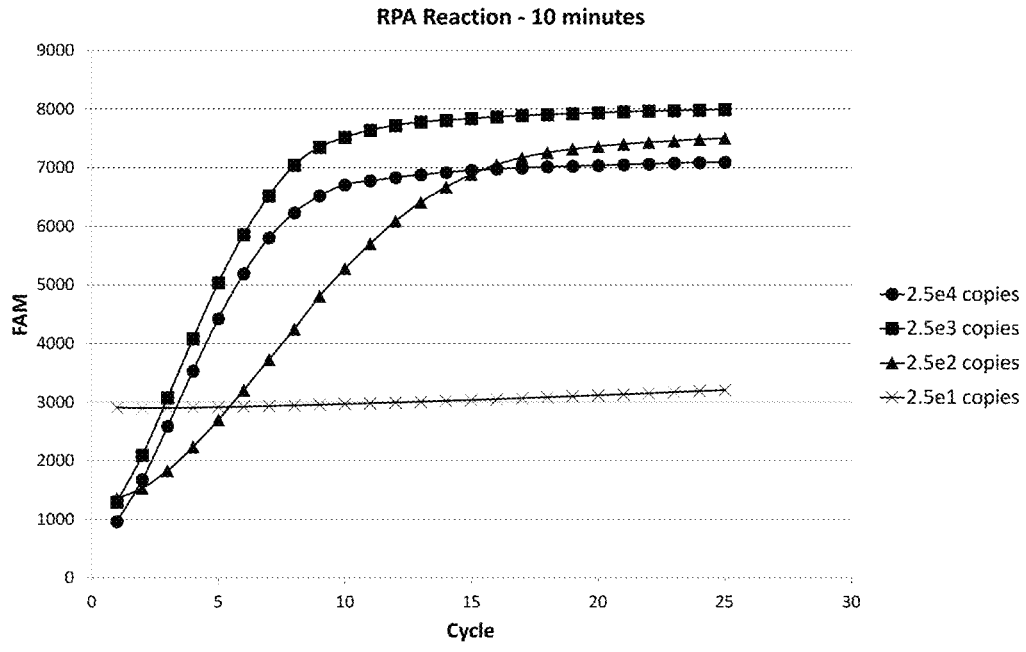
FIG. 5A-B illustrate the detection of RPA amplicons by FEN1 cleavage when starting with different amounts of RNA molecules, with the RPA reaction being carried out for about 10 min.
Figure 5B:
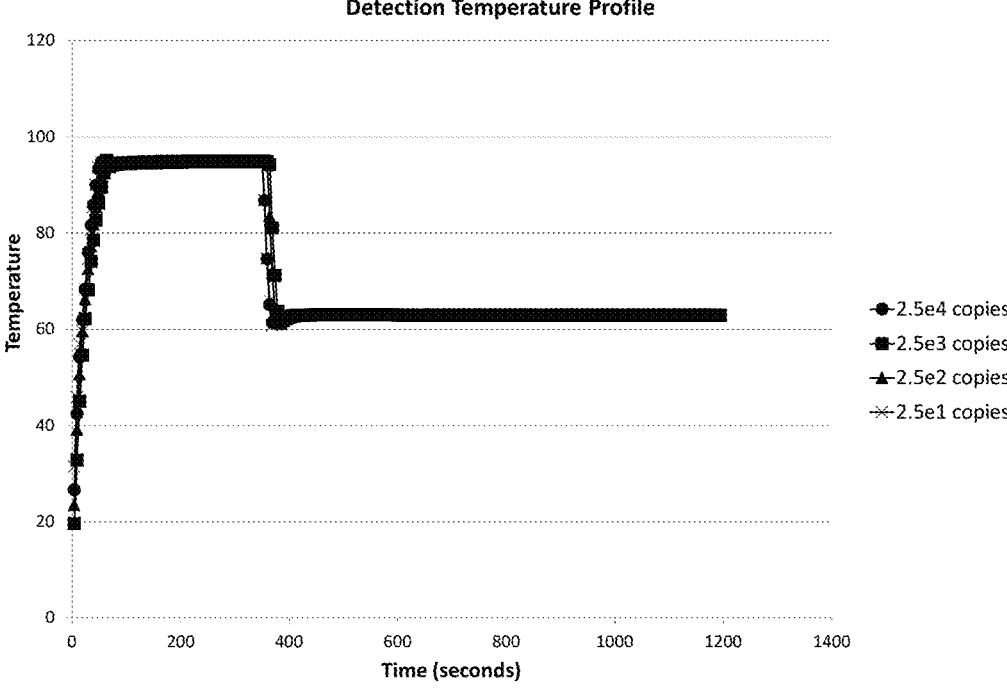

In order to further demonstrate the efficiency of the assay, RT-RPA reactions were set up using different amounts of RNA copies of the RdRP gene followed by FEN1 cleavage detection as described in the methods section above, with the RPA reaction being carried out for 10 minutes. As FIG. 5A illustrates, the nucleic acid amplification is still promptly detected, even using a lower amount of RNA ($2.5 \times 10^2$ RNA copies of the RdRP gene), and even at the reduced RPA reaction time. FIG. 5B maps out the denaturation step and the FEN1 cleavage detection reaction for each of the samples as functions of temperature and time.

Figure 6A:
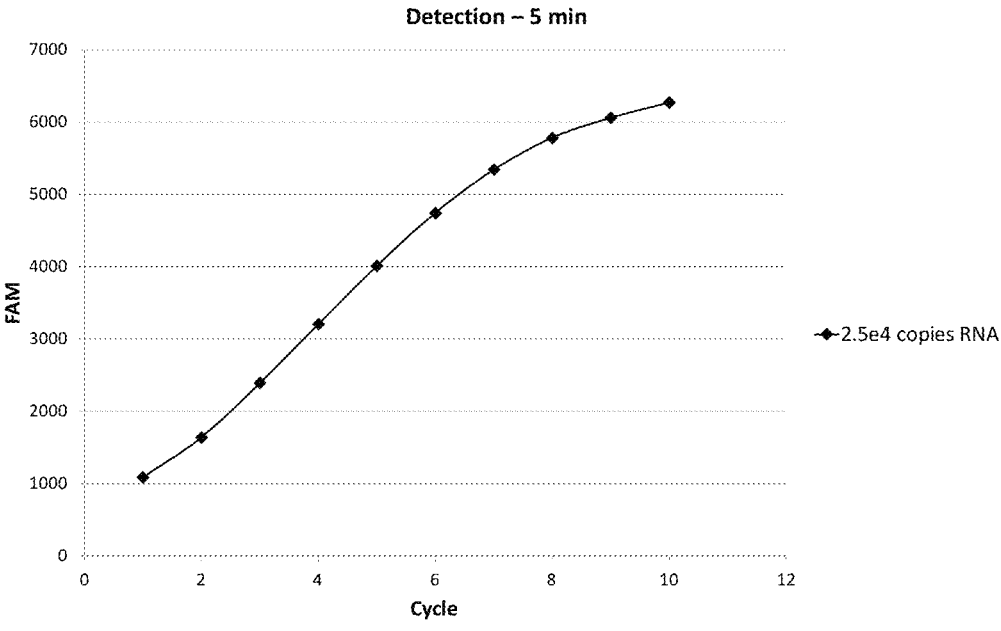
FIG. 6A-B illustrate the detection of RPA amplicons by FEN1 cleavage when starting with $2.5 \times 10^4$ copies of RNA molecules, with the FEN1 cleavage detection reaction being carried out for about 5 min.
Figure 6B:
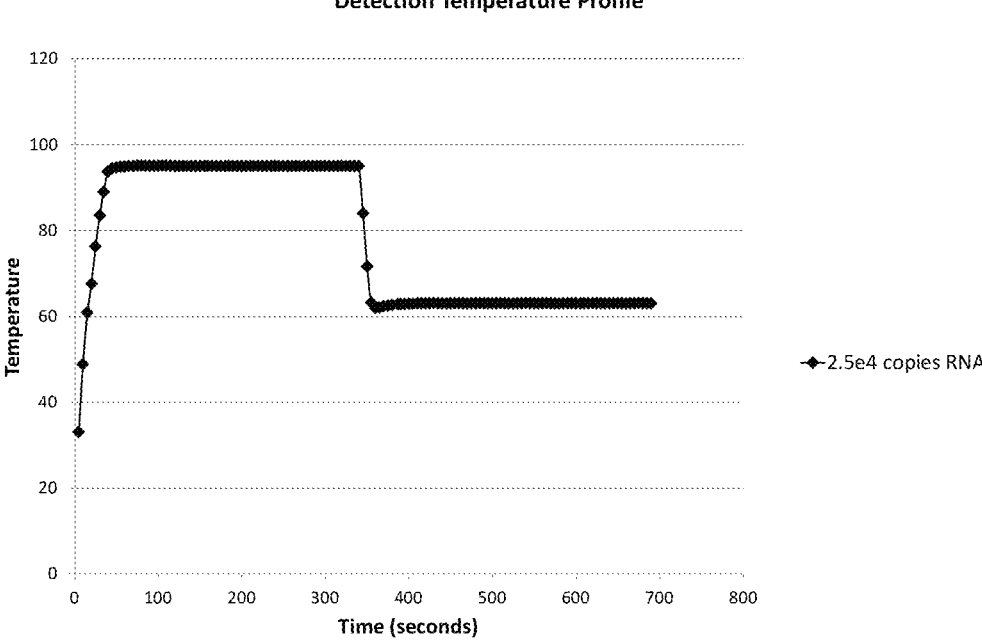

Moreover, FIG. 6A shows the detection of amplicons from an RT-RPA reaction set up using $2.5 \times 10^4$ RNA copies of the RdRP gene, wherein the FEN1 cleavage detection reaction time was reduced to 5 minutes. As observed, reduction of the FEN1 cleavage detection reaction time did not affect the detection of the RPA amplicons, demonstrating the strength of the assay. FIG. 6B maps out the denaturation step and the FEN1 cleavage detection reaction as functions of temperature and time.

Figure 7A:
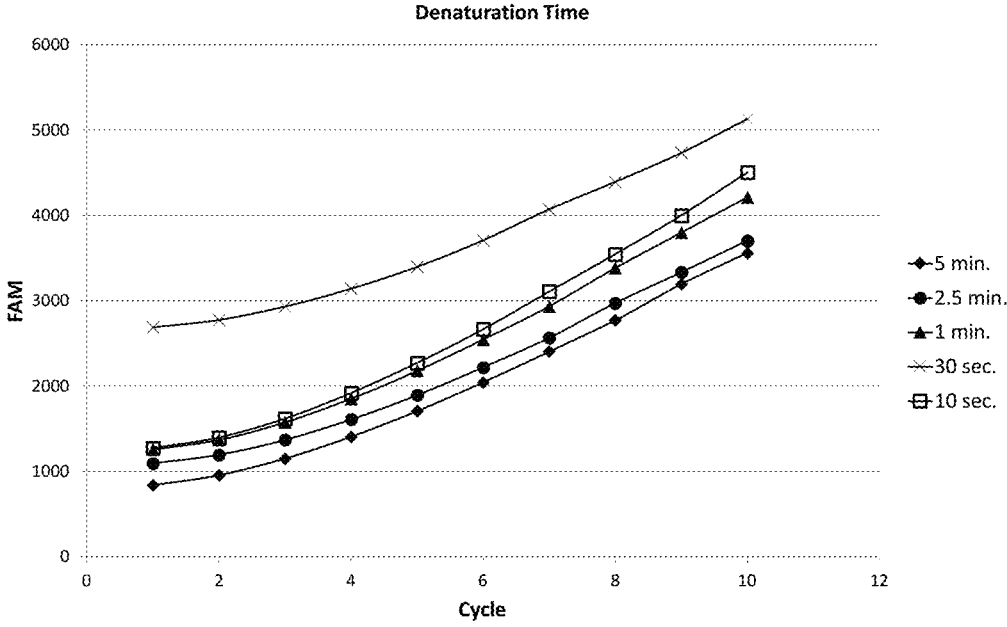
FIG. 7A-B illustrate the detection of RPA amplicons by FEN1 cleavage when starting with $2.5 \times 10^2$ copies of RNA molecules, with the denaturation step being carried out for about 5 minutes, 2.5 minutes, 1 minute, 30 seconds, or 10 seconds.
Figure 7B:
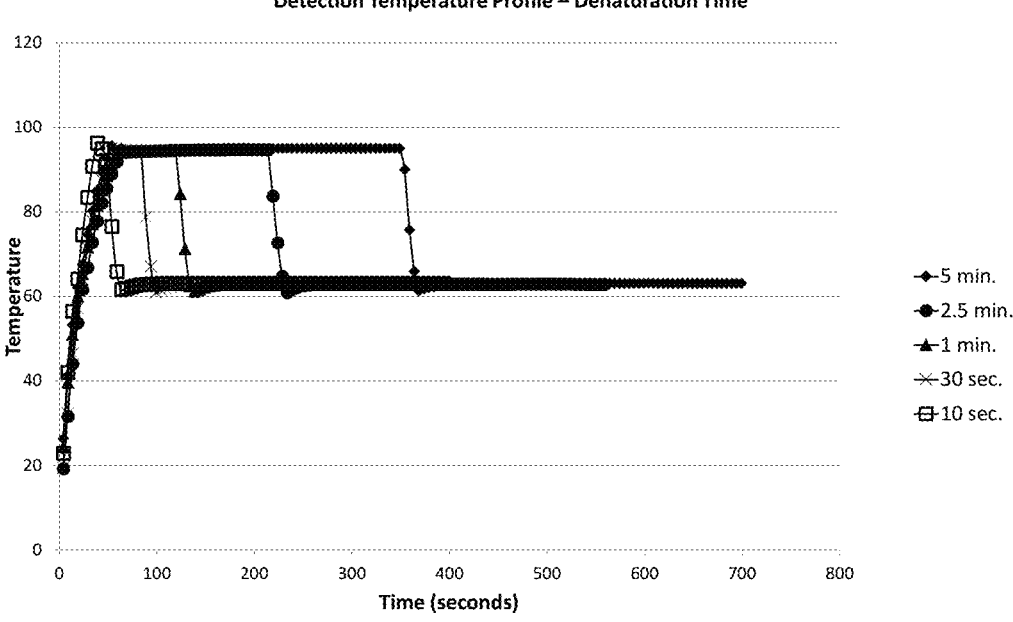

In order to test whether the denaturing step could be reduced in time without compromising the assay, RT-RPA reactions were set up using $2.5 \times 10^2$ RNA copies of the RdRP gene, wherein the denaturation step was reduced to 5 minutes, 2.5 minutes, 1 minute, 30 seconds, or 10 seconds, followed by an FEN1 cleavage detection reaction carried out for about 5 minutes. As FIG. 7A illustrates, even reducing the amount of time taken by the denaturing step does not compromise detection of the RPA generated amplicons by FEN1 cleavage. FIG. 7B maps out the denaturation step and the FEN1 cleavage detection reaction as functions of temperature and time.

Figure 10:
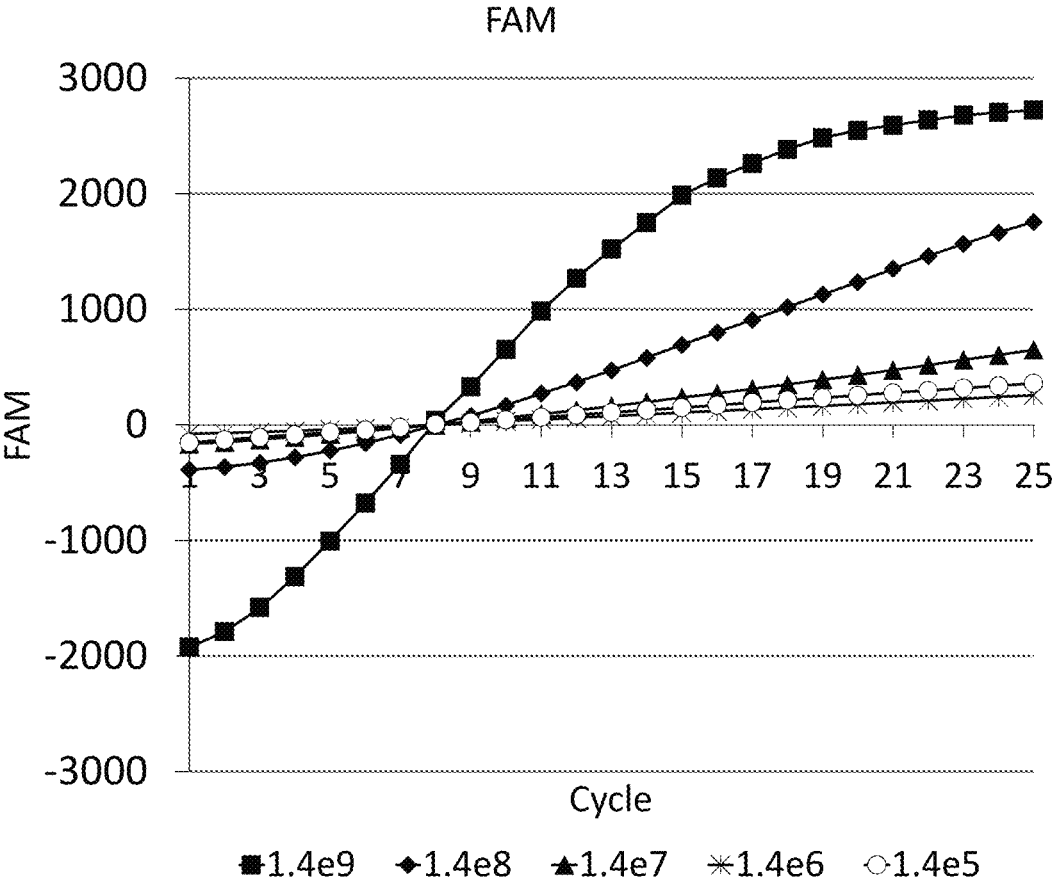
FIG. 10 illustrates a FEN1 cleavage detection reaction set up using standard samples comprising different copy numbers of DNA target template. Fluorescence was measured at every cycle, each cycle being 30 seconds long.

In order to determine the minimum amount of template needed to detect a signal during the FEN1 cleavage detection reaction, a reaction was set up using standards comprising synthetic double stranded DNA template. Each well comprised a different and predetermined copy number of the DNA template. The FEN1 detection reaction proceeded immediately at 63° C. following a 10 second denaturation step at 95° C. Fluorescence was measured at every cycle (each cycle is 30 seconds long). As depicted in FIG. 10 a signal can be detected in a sample containing $1.4 \times 10^8$ copies of the template as early as five minutes into the FEN1 cleavage detection reaction. Within 10 minutes, $1.4 \times 10^7$ copies is also detectable.

Figure 11:
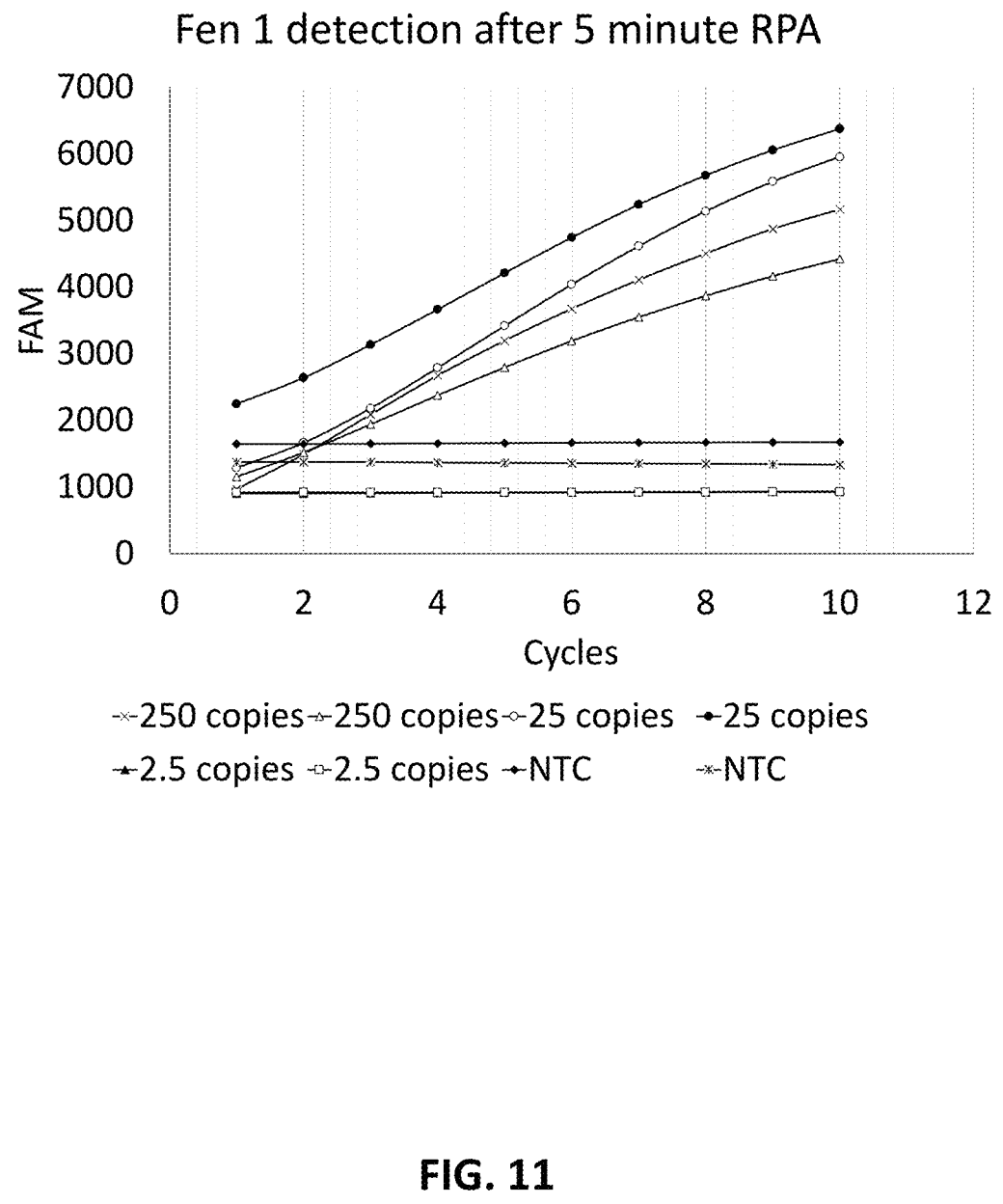

Additional studies aimed at demonstrating the sensitivity of the assay were performed. In FIG. 11 RT-RPA reactions were set up using different amounts of RNA copies of the RdRp gene followed by FEN1 cleavage detection as described in the methods section above, with the RPA reaction being carried out for 5 minutes. As FIG. 11 illustrates, the RPA reaction product is promptly detected in samples which resulted from RPA reactions set up with as little as 25 RNA copies of the SARS-Cov-2 RdRP gene. Positive reactions are distinguishable from non-template control (NTC) samples in less than a minute of the FEN1 cleavage run (each cycle is 30 seconds long).

Example 2

Methods:

RPA Reaction: An RPA reaction mix was prepared by rehydrating a pellet containing RPA proteins (a recombinase, a recombinase loading protein, a DNA binding protein) with 38 μL of rehydration buffer, and adding 0.5 μL each of 50 μM of forward and reverse primers (500 nM final concentration), 0.5 μL Superscript IV reverse transcriptase (100 units), and 1 μL RNase H (5 units). Superscript IV with RNase H enhanced sensitivity and reliability of the RPA reaction. Following rehydration, 1.4 μL 700 mM magnesium acetate was added to the mix (final concentration 19 mM) and vortexed to activate the reaction mix. RPA amplification reactions were set up by combining 8 μL of activated mix with 2 μL of sample to be tested. Small reaction volumes have been shown to decrease the need to mix RPA reactions for sufficient amplifications. The RPA amplification reactions were heated to 42° C. for 5-20 minutes for amplification.

FEN 1 Detection Reaction: 15 μL of detection mix was added to the 10 μL RPA amplification reaction to bring components to their correct final concentration for detection of the target-specific product of the amplification reaction. For a single reaction to detect both the N gene target and the internal control, components of the detection mix were as follows:

4.18 μL water 0.3 μL 50×PCR buffer (1 M Tris pH 8.4, 2.5 M KCl)

0.27 μL 280 mM MgOAc 0.5 μL of 10 μM N3 initiator oligo N3_IO_2

0.25 μL of 100 μM N3 FEN1 probe N3_IO_IP_2

0.5 μL of 10 μM IC initiator oligo IC11 RPA R-1

0.25 μL of 100 μM IC FEN1 probe IC11 IO_IP_2

1.25 μL of 10 μM N3 FEN1 reporter INV-UR A2

0.5 μL of 10 μM IC FEN1 reporter INV-UR C1

7 μL thermostable FEN1 enzyme (224 units)

INV-UR A2 allows detection of the N gene target of SARS-CoV-2 in the FAM channel while the internal control is detected by fluorescence derived from the INV-UR C1 reporter in CFR.

Thermoptical (RT-RPA reaction+FEN1 cleavage detection reaction): For the RT-RPA reaction, the reaction is brought to 42° C. for 5-20 minutes. Following amplification, the FEN1 cleavage detection mix is combined with a sample of the RT-RPA reaction product. Then, this reaction is brought to 95° C. for as little as 1 second (denaturation step) before the fluorescence signal is detected at 63° C., indicating the presence of the amplified product. Intervals at which the fluorescence was read for detection were 30 seconds in length (each cycle is 30 seconds) but they can likely be shortened.

The present invention is not limited to these examples. Small amounts of amplification reaction may also be added to a larger detection mix with equally sensitive results for detection.

Targeting the SARS-CoV-2 N Gene (N3 Assay)

Figure 19A:
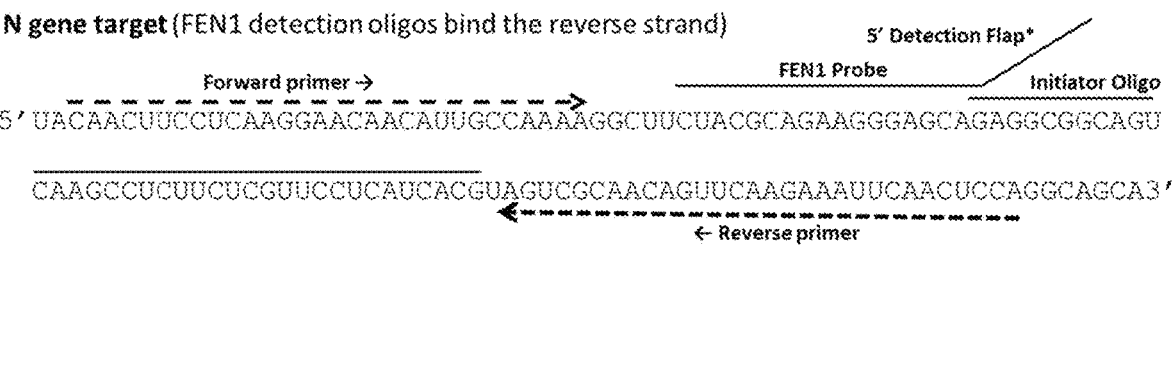
FIG. 19A-B illustrate the design of and binding regions for RPA primers and FEN1 cleavage probes and oligos used for targeting of the SARS-CoV-2 N gene and the internal control template for amplification and detection.
Figure 19B:
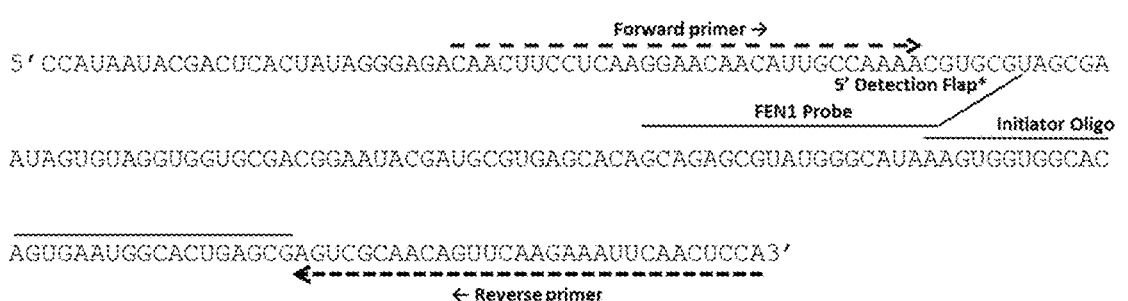

High amounts of the N gene are found in SARS-CoV-2 positive samples in comparison to other targeted genes in SAR-CoV-2. The SARS-CoV-2 N gene was used as the target for this assay, which measured the presence of the N gene via RPA and FEN1 cleavage detection reactions. The reliability of this assay is enhanced by the use of an internal control template. This is an internal control RNA template sequence, which is amplified by the same primers used to amplify the N gene. This allows only one set of primers to be used and greatly enhances the ability to multiplex an assay with an internal control, averting the need to add another set of primers that would interfere with target amplification. RPA allows for the amplification of the N gene target and a region of the internal control template. The products of these parallel amplifications are detected through a FEN1 cleavage detection reaction using different fluorescence reporters for the N gene target and the internal control. FIG. 19A illustrates, within the N gene sequence, the region corresponding in sequence to the N Forward Primer (N3_F1), and the regions where the N Reverse Primer (N3_R1), the FEN1 probe oligonucleotide (N3_IO_IP_2), and the initiator oligonucleotide (N3_IO_2) would anneal on N gene sequence. FIG. 19B illustrates, within the internal control template, the region corresponding in sequence to the N3_F1 primer (which would anneal to the complementary strand), and the regions where the N3_R1 primer, the FEN1 probe oligonucleotide (IC11 IO_IP_2C), and the initiator oligonucleotide (IC11 RPA R-1) would anneal on N gene sequence.

Figure 12:
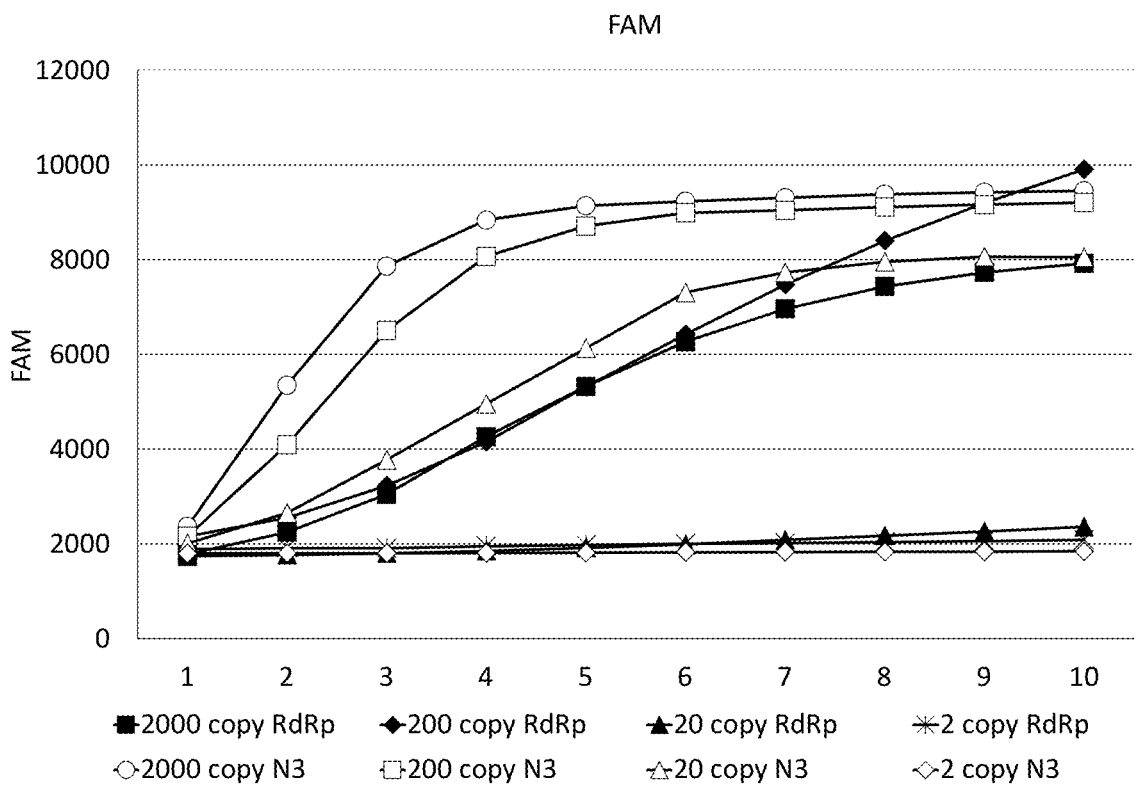
FIG. 12 illustrates a comparison in sensitivity between the N3 assay and the RdRp assay. Fluorescence was measured at every cycle, each cycle being 30 seconds long.

To compare the sensitivity of the N3 assay and the RdRp assay, RT-RPA reactions were set up using different amounts of RNA copies of the RdRP gene, and different amounts of RNA copies of the N gene. The RPA reaction was carried out for 20 minutes, followed by FEN1 cleavage detection reaction as described in the methods sections above. As FIG. 12 illustrates, the N3 assay is more sensitive than the RdRp assay.

Figure 13A:
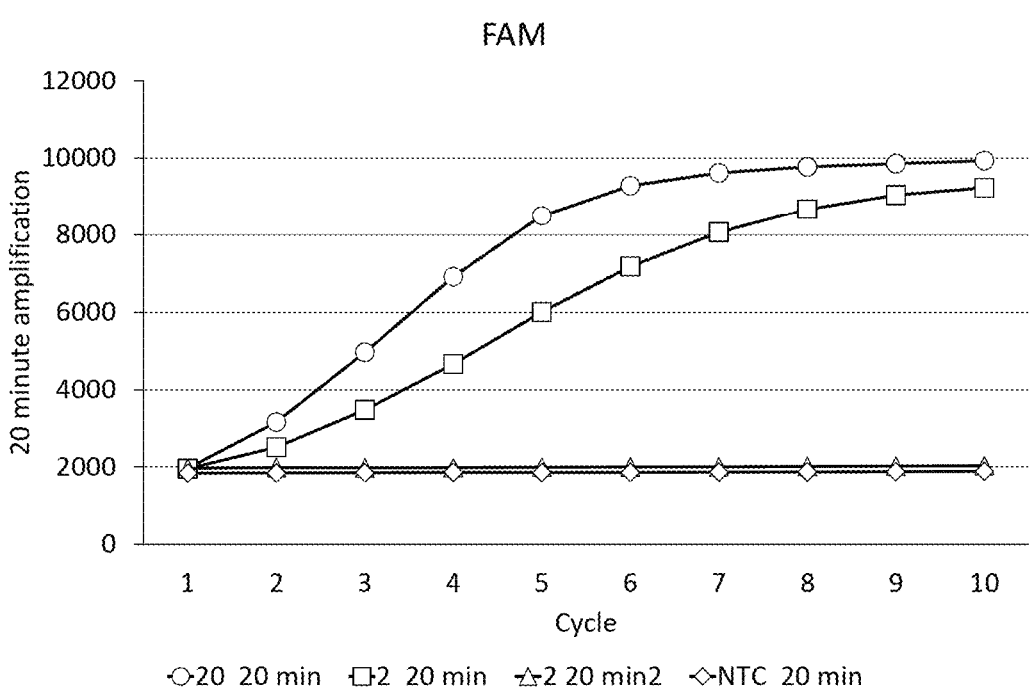
FIG. 13A illustrates the FEN1 cleavage detection of the N gene target after an RT-RPA reaction was carried out for 5 minutes versus 20 minutes.
Figure 13B:
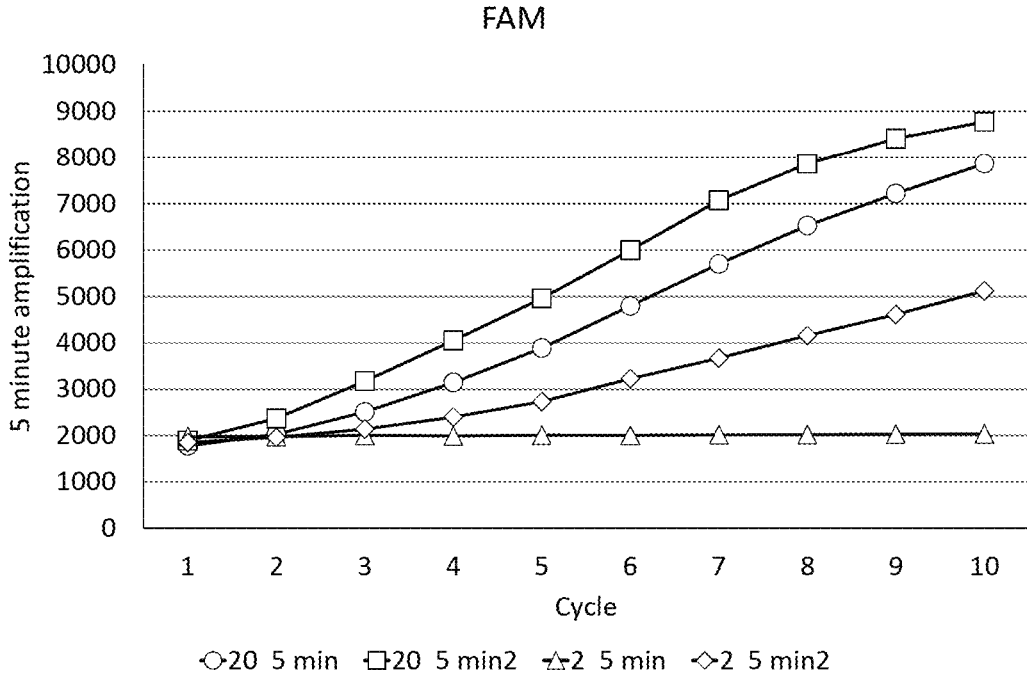
FIG. 13B illustrates the FEN1 cleavage detection of the N gene target after an RT-RPA reaction was carried out for 5 minutes. Fluorescence was measure at every cycle, each cycle being 30 seconds long.

Further development of the N3 assay also demonstrated the assay's enhanced sensitivity even if the RT-RPA amplification is carried out for as little as 5 minutes. FIGS. 13A-13B illustrate an experiment comparing the FEN1 cleavage detection of the N gene target after an RT-RPA reaction was carried out for 5 minutes versus 20 minutes. Fluorescence indicating the presence of the amplified N gene is effectively measured even in RT-RPA reactions carried out for only 5 minutes.

Figure 14:
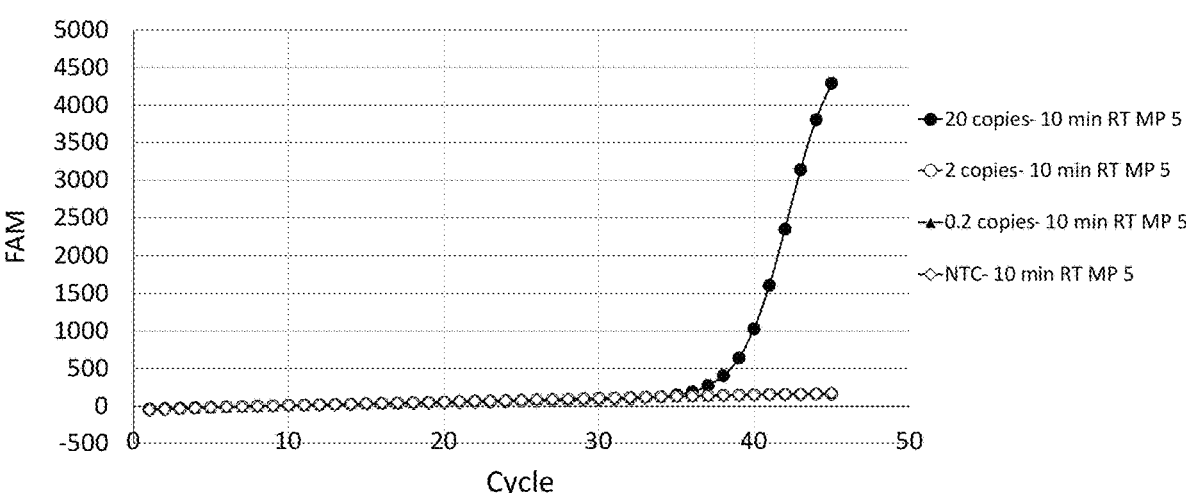
FIG. 14 illustrates a comparison between the N3 assay and PCR amplification as measured using a hydrolysis probe.

Additional experiments also show that the N3 assay sensitivity is comparable to the sensitivity of detection of the RdRp gene by PCR. In the experiment illustrated in FIG. 14, genomic RNA was used as template for an RdRp gene-PCR and the N3 assay. Detection of the PCR product was done using a hydrolysis probe. The N3 assay reliably detected 20 copies of the RNA target, and often even detected as low as 2 copies in the sample.

Figure 15:
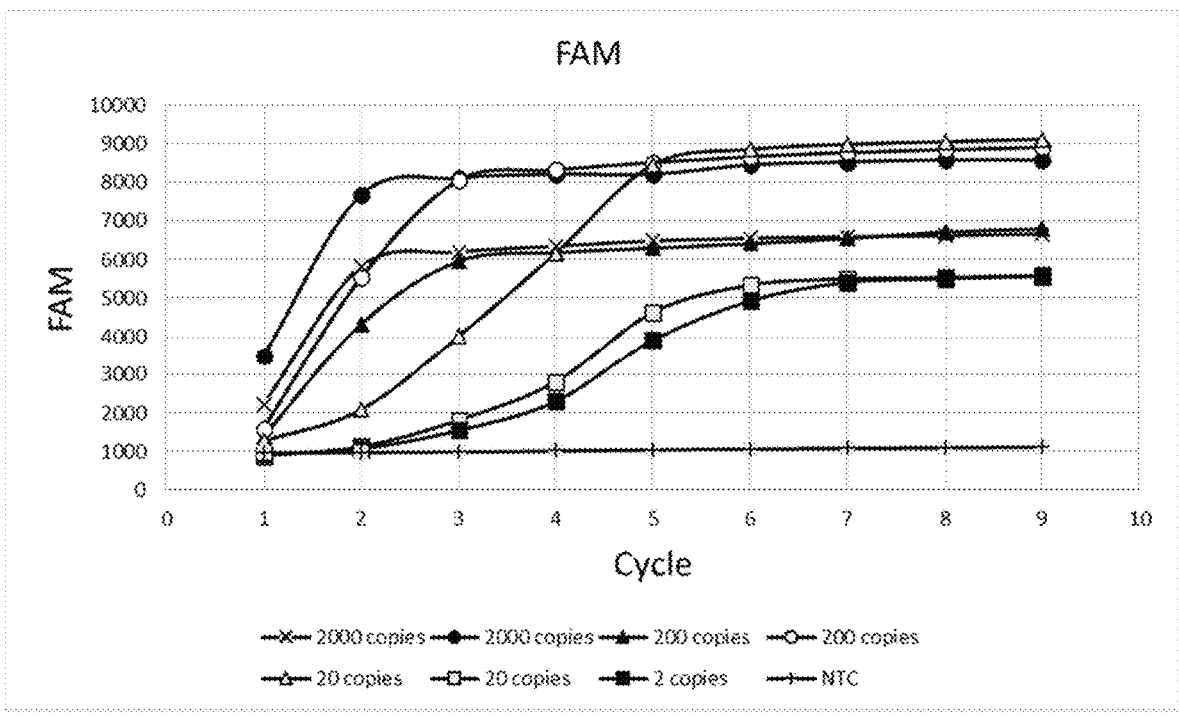
FIG. 15 illustrates the use of the N3 assay to detect its target in contrived nasal samples in normal saline. Each sample contains a different copy number of the RNA target. An RT-RPA reaction was carried out, and fluorescence was measured during the FEN1 cleavage detection reaction at every cycle, each cycle being 30 seconds long.

The N3 assay detects its target in contrived nasal samples in normal saline. Contrived samples were created by placing a nasal swab in 1 mL normal saline (0.85%) and adding 1 U/uL RNase inhibitor before making dilutions of viral genomic RNA. In FIG. 15 each sample contains a different copy number of the RNA target. The sensitivity and speed of amplification and detection was maintained.

Figure 16A:
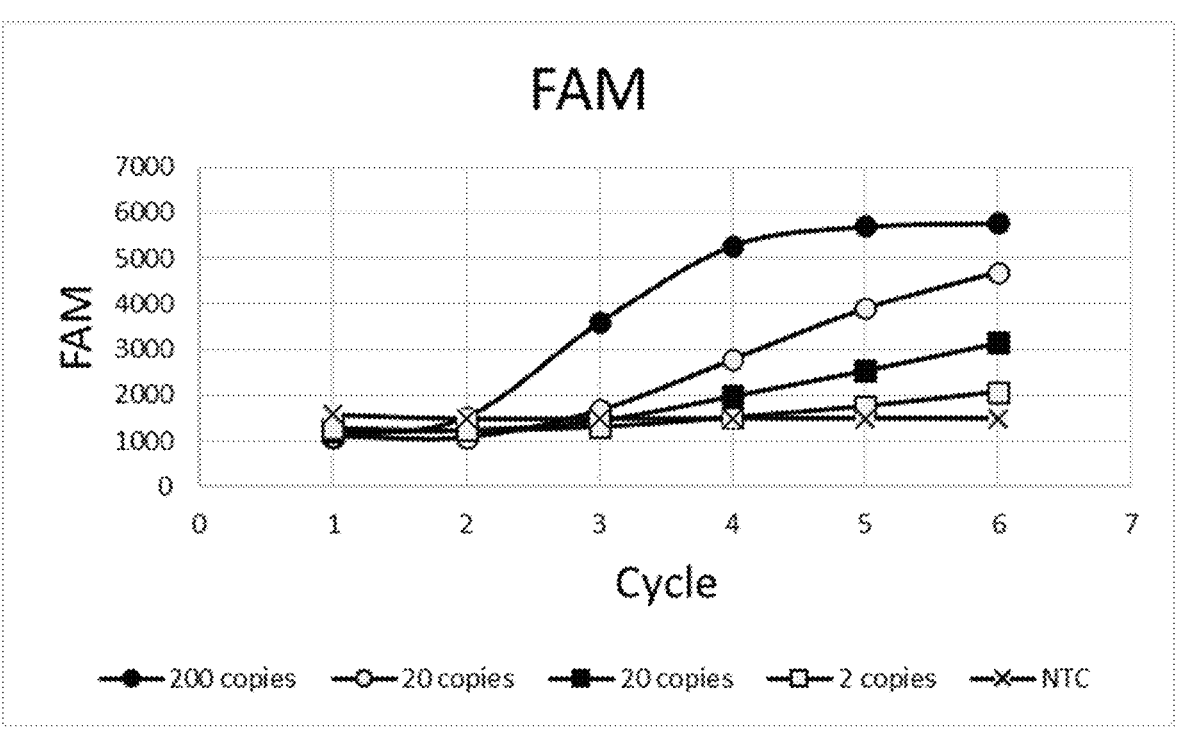
FIG. 16A-B illustrate an N3 assay where detection time has been shortened to under 4 minutes. Detection of the target gene can be observed within 1 cycle (30 seconds) of the FEN1 cleavage detection reaction. Fluorescence was measured at every cycle, each cycle being 30 seconds long.
Figure 16B:
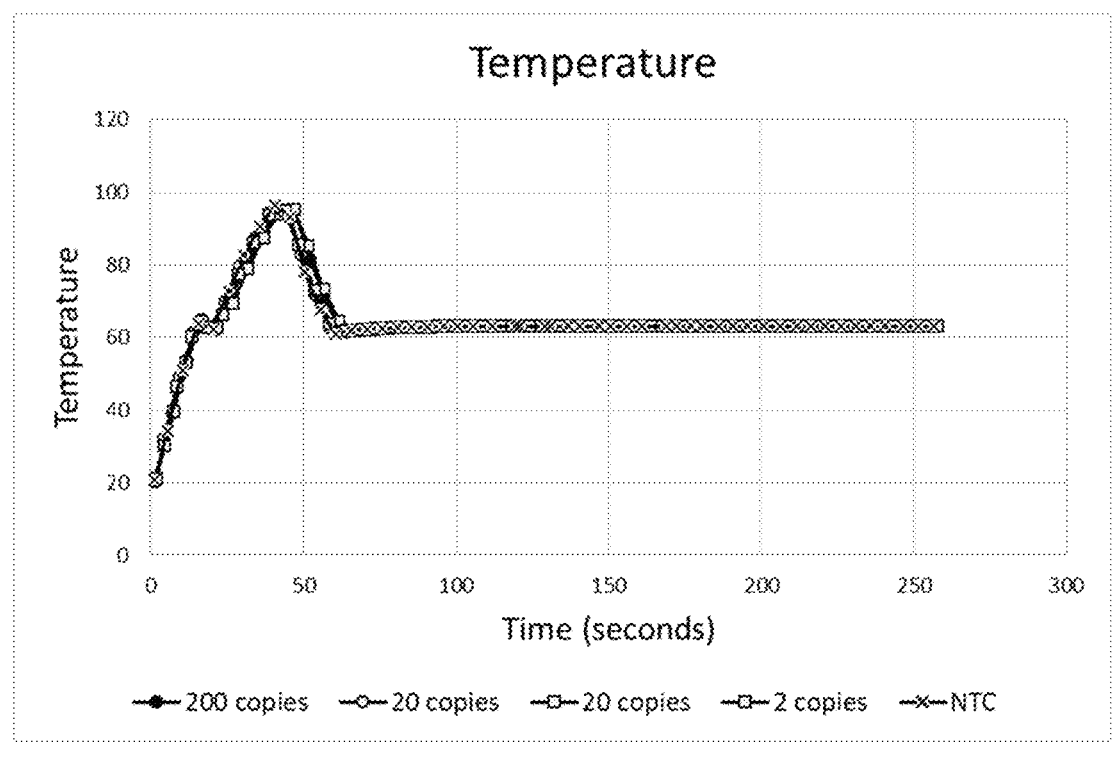

Additionally, FIG. 16A shows that the detection in the N3 assay is accomplished in under 5 minutes. Previous runs detected the target amplicon in about 6 minutes. In these experiments a clear detection took as little as 30 seconds once fluorescence measurements were taken. Each sample contains a different copy number of the targeted RNA. An improved thermoptical program shows detection in about 4 minutes or less is easily possible. FIG. 16B maps out the denaturation step and the FEN1 cleavage detection reaction for each of the samples as functions of temperature and time.

Figure 17A:
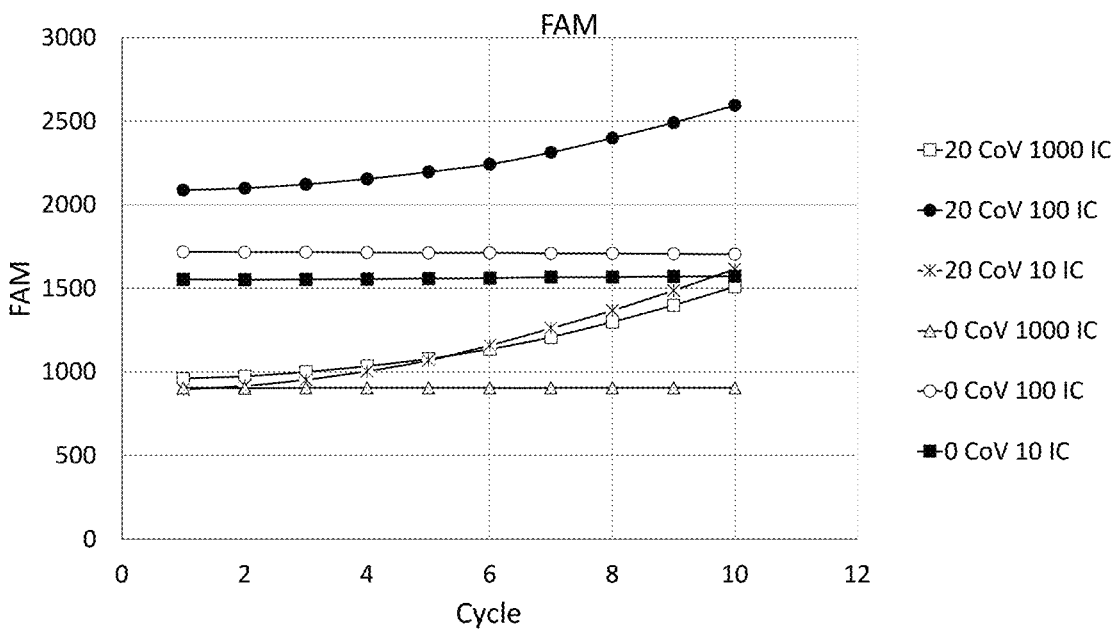
FIG. 17A-B illustrate the development of an internal control for the N3 assay. Each sample contained a different copy number for the N gene or the internal control template. An RT-RPA reaction was carried out, and fluorescence was measured during the FEN1 cleavage detection reaction at every cycle, each cycle being 30 seconds long.
Figure 17B:
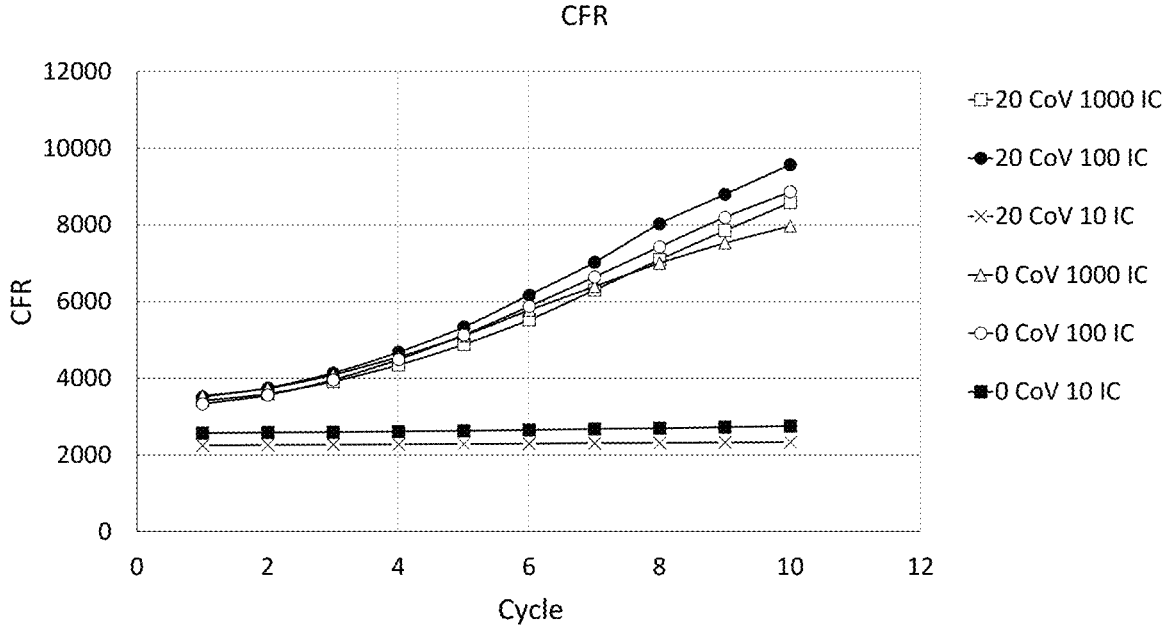

FIG. 17A-B illustrate the development of an internal control for the N3 assay. Each sample contained a different copy number for the N gene or the internal control template. The internal control was developed to be amplified with the same primers used for amplification in the N3 assay. Due to the specificity of the FEN1 cleavage detection reaction, amplicons can be easily detected and differentiated in a single detection step where the target gene can be detected in the FAM fluorescence channel, and the internal control (IC) target in the CFR fluorescence channel.

Figure 18A:
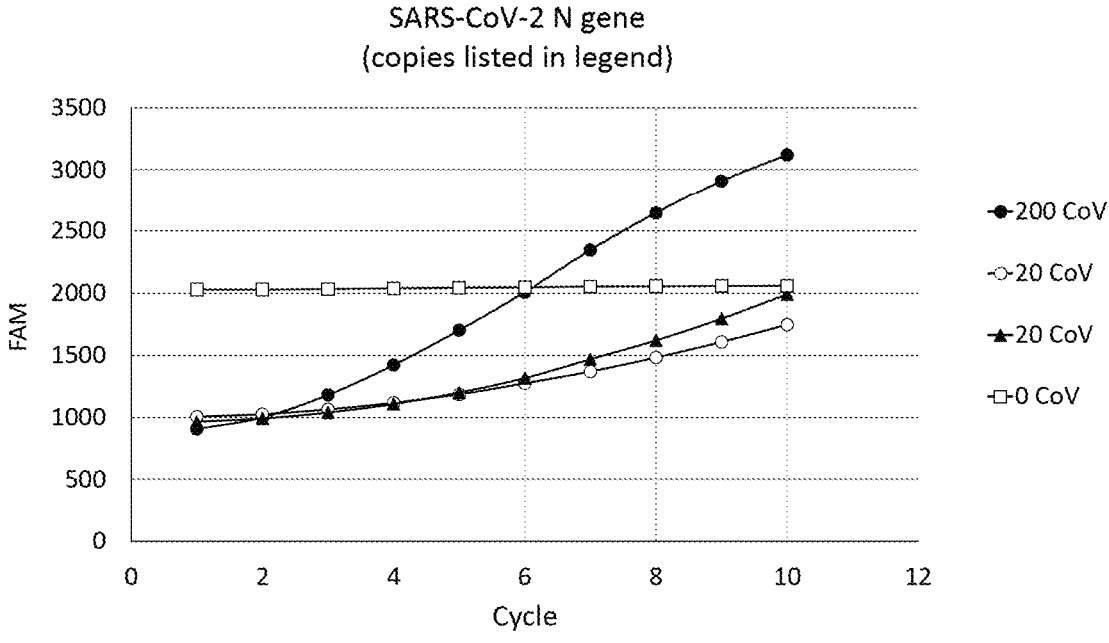
FIG. 18A illustrates the amplification and detection of the N gene target.
Figure 18B:
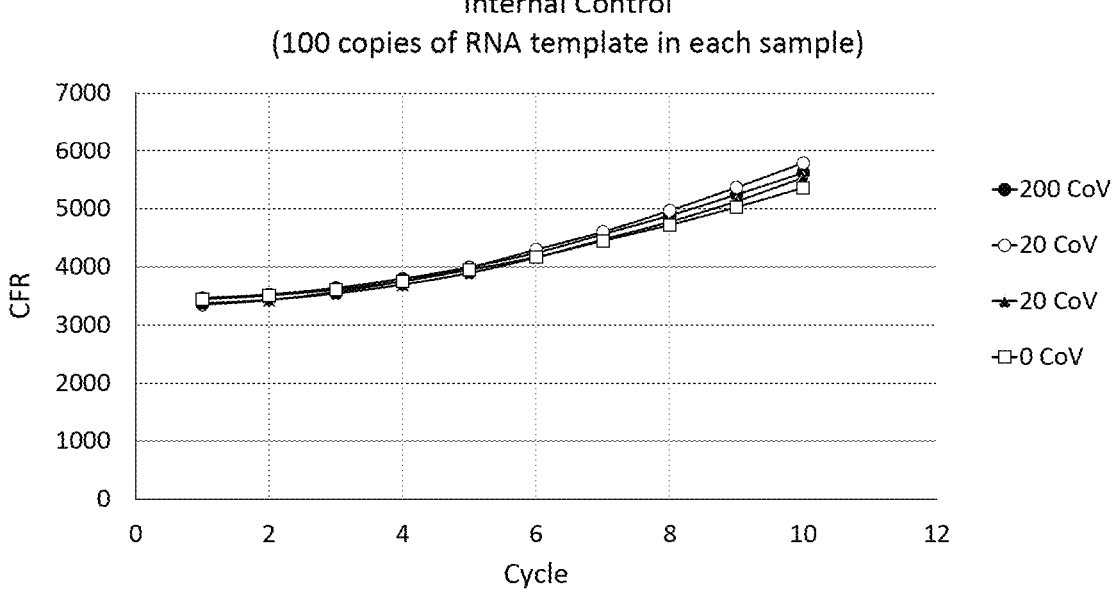
FIG. 18B illustrates the simultaneous amplification and detection of the internal control target within the same sample. The samples had different starting copy numbers for the N gene but each had 100 copies of the internal control RNA template. An RT-RPA reaction was carried out, and fluorescence was measured during the FEN1 cleavage detection reaction at every cycle, each cycle being 30 seconds long.

FIGS. 18A-18B further illustrate the simultaneous amplification and detection of the N gene target and the IC target within the same sample. Fast, sensitive amplification and detection reactions were maintained due to the custom internal control. Samples diluted in normal saline were still viable. Therefore, these studies demonstrated the sensitivity and efficacy of the N3 assay.

A variety of further modifications and improvements to the systems, methods, and devices of the present invention will be apparent to those skilled in the art. Accordingly, no limitation on the invention is intended by way of the foregoing description and accompanying drawings, except as set forth in the appended claims. The foregoing description has been presented for purposes of illustration. It is not exhaustive and is not limited to precise forms or embodiments disclosed. Modifications and adaptations of the embodiments will be apparent from consideration of the specification and practice of the disclosed embodiments. In addition, while certain reagents, components, and arrangements have been described, other reagents, components, and arrangements may be implemented, as will be appreciated from this disclosure.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

Example 3

In some embodiments, instead of RPA, a Strand Displacement Amplification (SDA) reaction is used to amplify a nucleic acid target, wherein the amplified target is detected by the FEN1 cleavage detection reaction. SDA is an isothermal, in vitro nucleic acid amplification technique which relies on a strand displacement DNA polymerase and a DNA nicking event targeted via primer design and a nicking endonuclease.

Materials and Methods

SDA reactions were set up by first preparing a master mix for 8.5 reactions as follows:

TABLE 1

| SDA reaction master mix | | | |
|---|---|---|---|
| Reagent | Stock | Final | Volume (μL) |
| Water | | | 111.46 μL |
| 10x Thermopol Buffer (NEB) | 10 X | 1.0 X | 21.25 μL |

TABLE 1-continued

SDA reaction master mix

| Reagent | Stock | | Final | | Volume (µL) |
|---|---|---|---|---|---|
| dNTPs | 10 | mM | 0.4 | mM | 8.50 µL |
| NaCl | 1000 | mM | 100.0 | mM | 21.25 uL |
| Bst 3.0 | 8 | U/uL | 0.3 | U/uL | 7.97 µL |
| N.BstNBI | 10 | U/uL | 2.00 | U/rxn | 1.70 µL |
| gp32 | 10 | ug/uL | 10.00 | ug/rxn | 8.50 uL |
| Bumper-F1 | 10 | uM | 0.05 | uM | 1.06 uL |
| Bumper-R1 | 10 | uM | 0.05 | uM | 1.06 uL |
| RdRp-R2-SDA | 10 | uM | 0.2 | uM | 4.25 uL |
| RdRp-F2-SDA | 10 | uM | 0.2 | uM | 4.25 µL |
| | | | | Total | 191.25 µL |

Enzymes (Bst 3.0, N.BstNBI, and gp32) were added immediately before initiating the reaction. 22.5 µL of the SDA reaction mix was added to each tube along with 2.5 µL of sample for a 25 µL total reaction. The sample in each tube constituted different copy numbers of RdRp Gblock DNA and a control (NTC). The reactions were run for 10 minutes at 57° C. After amplification, the reactions were stopped by bringing the temperature to 95° C. for 4 minutes.

A FEN1 cleavage detection reaction mix for 8.5 reactions was prepared as follows (using a thermostable FEN1 enzyme):

| Reagent | Stock | | Final | | Volume (µL) |
|---|---|---|---|---|---|
| Water | | | | | 130.08 µL |
| Glycerol | 50.00 | % | 10.00 | % | 17.00 uL |
| 50x PCR buffer | 50 | X | 1.0 | X | 4.25 µL |
| MgOAc | 280 | mM | 5.0 | mM | 3.79 µL |
| nCov_IO_2 | 10 | uM | 0.2 | uM | 4.25 µL |
| nCov_IO_IP_2 | 100 | | 1.0 | | 2.13 µL |
| INV-UR A2 | 10 | uM | 0.2 | uM | 4.25 µL |
| FEN1 | 3.00 | uL/rxn | | | 25.50 µL |
| | | | | Total | 191.25 µL |

Figure 20:
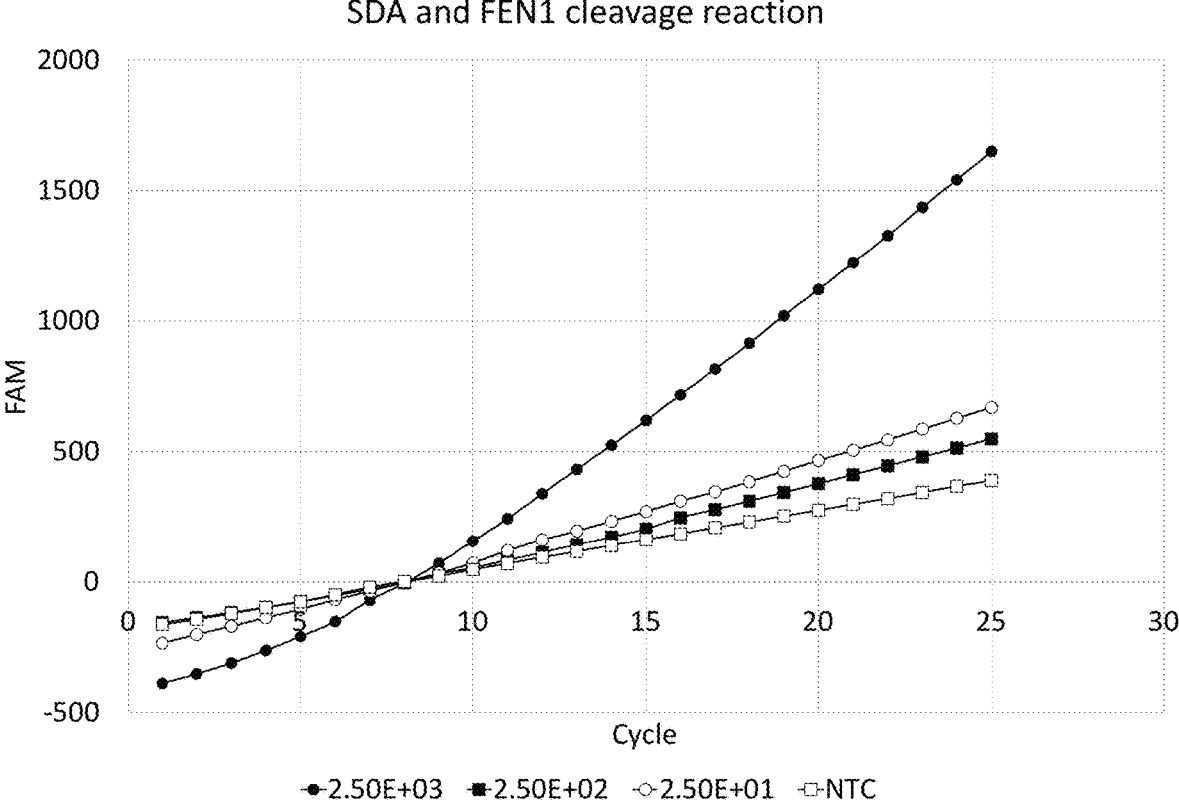
FIG. 20 illustrates the detection of the SARS-CoV-2 RdRp gene in samples containing different copies of the gene by a FEN1 cleavage detection reaction after nucleic acid amplification by SDA.

To detect the SDA amplified product, 2.5 µL of a completed SDA reaction was added to a 22.5 uL of the FEN1 cleavage detection reaction mix for a final volume of 25 µL (same as with the RPA essays). The FEN1 cleavage detection reaction was run by bringing the reaction to 95° C. for as little as 1 second (denaturation step) before the fluorescence signal was detected at 63° C., indicating the presence of the amplified product. Intervals at which the fluorescence was read for detection were 30 seconds in length (each cycle is 30 seconds) (FIG. 20).

Example 4

As proof of principle that an RPA reaction could be run and the amplified product detected by a FEN1 cleavage detection reaction at a time not immediately after the RPA run, an experiment was done where the RPA reactions were run on day 1, and the amplified nucleic acid products were detected on day 2 by a FEN1 cleavage detection reaction (using a thermostable FEN1 enzyme).

RPA reactions were set up and run at 200 copies of positive control SARS-CoV-2 RNA along with 1000 copies of internal control template (IC) or NTC.

Figure 21A:
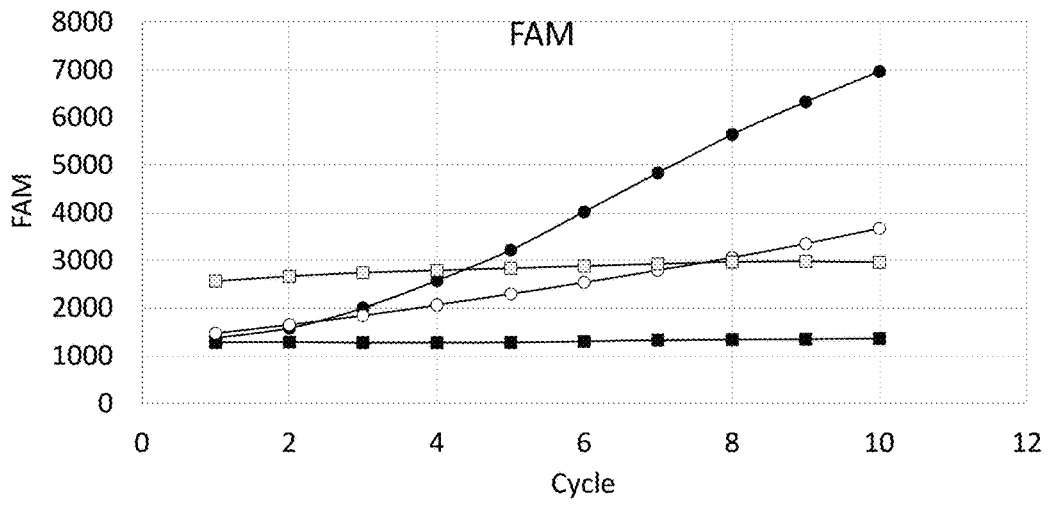
FIG. 21A-B illustrate experiments where RPA was run on day 1 and the amplified products were detected on day 2 by FEN1 cleavage detection reaction.
Figure 21B:
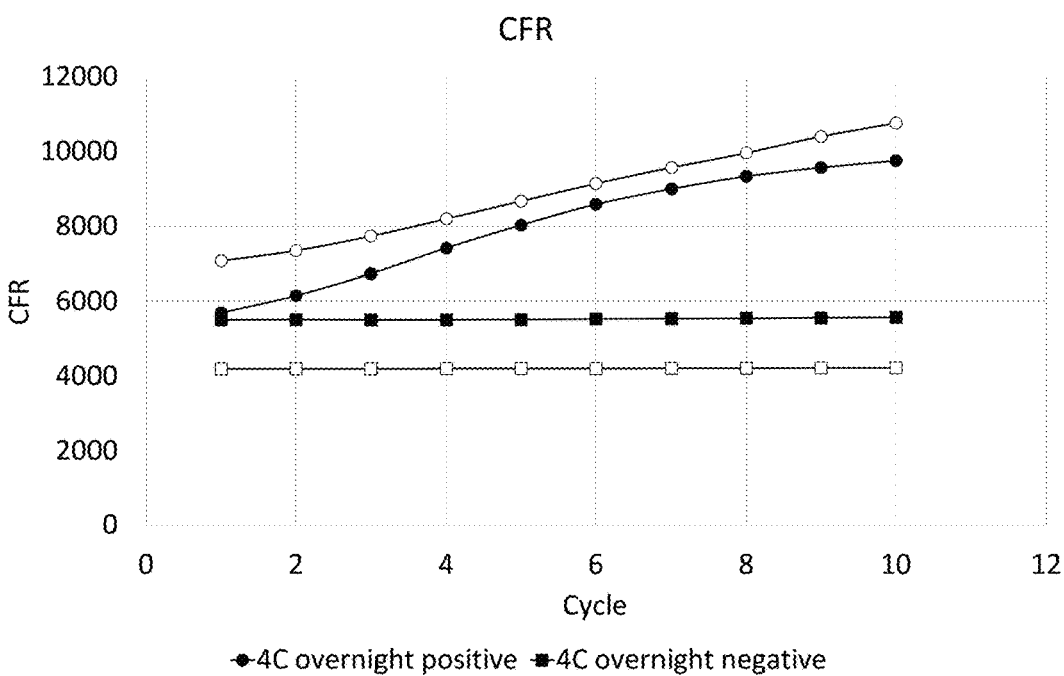

The completed RPA reaction and FEN1 cleavage detection reaction were kept at either room temperature or 4° C. overnight separately. The next day the reactions were combined and the product of the RPA was detected by the FEN1 cleavage detection reaction. In FIG. 21, Panel A illustrates the detection of the N gene target of SARS-CoV-2 (FAM), and Panel B illustrates the detection of the IC (CFR). The results show that the assay retains sensitivity for both the target and IC after the amplification is stored either at 4° C. or room temperature overnight. This greatly enhances the flexibility of the assay, potentially allowing amplification to happen at one location and rapid detection to happen at another.

Example 5

As proof of principle that an RPA reaction could be run and the amplified product detected by a FEN1 cleavage detection reaction within the same vessel or tube, two experiments were set up wherein the reagents for a reverse transcription (RT) reaction, an RPA reaction, and a FEN1 cleavage detection reaction were placed in the same tube with the starting target nucleic acid.

In the first experiment, a tag target nucleic acid was amplified by RPA and the amplified product detected by FEN1 cleavage after the reaction was set up as follows

| | | Stock Conc | | Final conc. | | Volume (uL) |
|---|---|---|---|---|---|---|
| Formulation of Master Mix: | | | | | | |
| Forward Primer | IC11 RPA F-1 | 50 | uM | 0.5 | uM | 0.5 |
| Reverse Primer | IC11 RPA R-1 | 50 | uM | 0.5 | uM | 0.5 |
| IC11 flap probe | IC11_IO_IP_2C_C3 | 10 | uM | 0.1 | uM | 0.5 |
| CFR Reporter | INV UR-C1 | 10 | uM | 0.2 | uM | 1 |
| FEN1 | | 1.5 | uL/rxr | | | 7.5 |
| Rehydration Buffer | | | | | | 38 |
| | Total Volume | | | | | 48 |
| Formulation in each tube | | | | | | |
| Volume of 700 mM MgAc to Add/Tube | | | | | | 1.4 uL |
| master mix | | | | | | 8 uL |
| template | | | | | | 2 uL |

Figure 22:
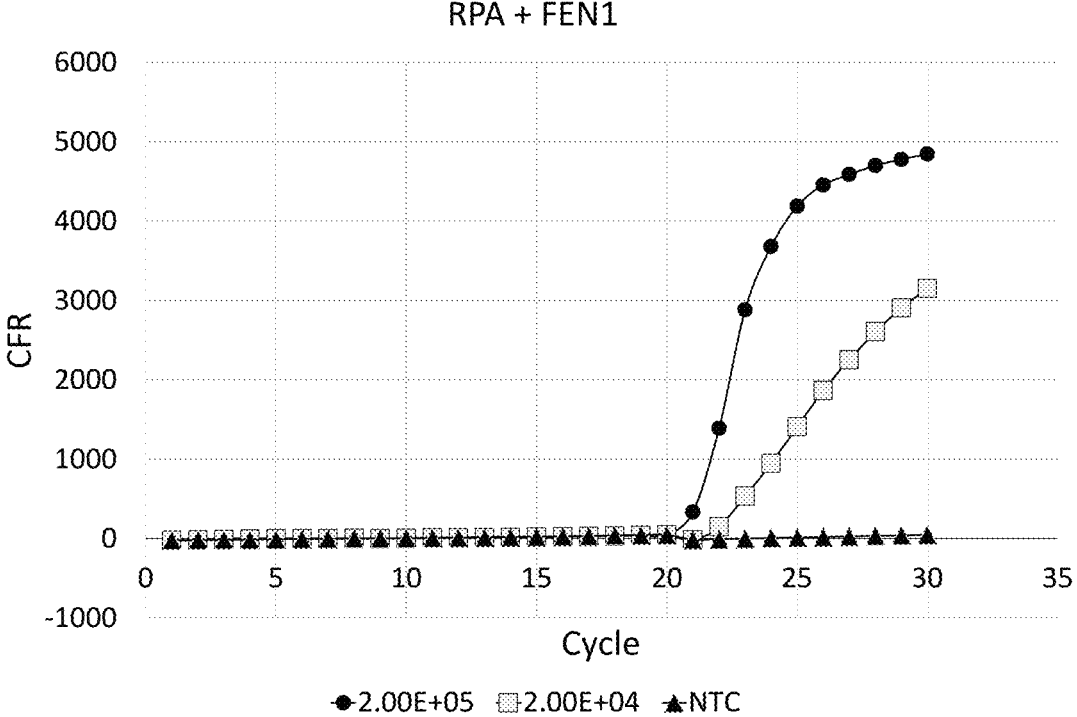
FIG. 22 illustrates an experiment where an RPA reaction and a FEN1 cleavage detection reaction were carried out within the same vessel or tube by combining all RPA, and FEN1 cleavage reaction reagents together with the target nucleic acid.

The amplification was performed for 10 minutes at 42° C. Following amplification, the reaction was brought to 95° C. for as little as 1 second (denaturation step) before the FEN1 reaction-generated fluorescence signal was detected at 63° C., indicating the presence of the amplified product. Intervals at which the fluorescence was read at baseline during amplification and during detection were 30 seconds in length (each cycle is 30 seconds). The fluorescence signal was detected starting at around 20 cycles, immediately following amplification, in the samples containing $2 \times 10^5$ or $2 \times 10^4$ copies of the tag target nucleic acid (FIG. 22).

In the second experiment, target nucleic acid was the internal control sequence (IC) of the N3 assay. The RNA target was reverse transcribed, amplified by RPA, and the amplified product detected by FEN1 cleavage. The reaction was set up as follows:

| | | Stock Conc | | Final conc. | | Volume (uL) |
|---|---|---|---|---|---|---|
| Formulation of Master Mix: | | | | | | |
| Forward Primer | N3_F1 | 50 | uM | 0.5 | uM | 0.5 |
| Reverse Primer | N3_R1 | 50 | uM | 0.5 | uM | 0.5 |
| IC11N3 flap probe | IC11N3_IO_IP_4a | 100 | uM | 1 | uM | 0.5 |
| CFR Reporter | INV UR-C1 | 10 | uM | 0.2 | uM | 1 |
| RNAse H | | | | | | 1 |
| Superscript IV | | 0.5 uL/tube | | | | 0.5 |
| FEN1 | | 1.5 uL/rxr | | | | 7.5 |
| Rehydration Buffer | | | | | | 38 |
| | Total Volume | | | | | 49.5 |
| Formulation in each tube: | | | | | | |
| Volume of 700 mM MgAc to Add/Tube | | | | | | 1.4 uL |
| master mix | | | | | | 8 uL |
| template | | | | | | 2 uL |

Figure 23:
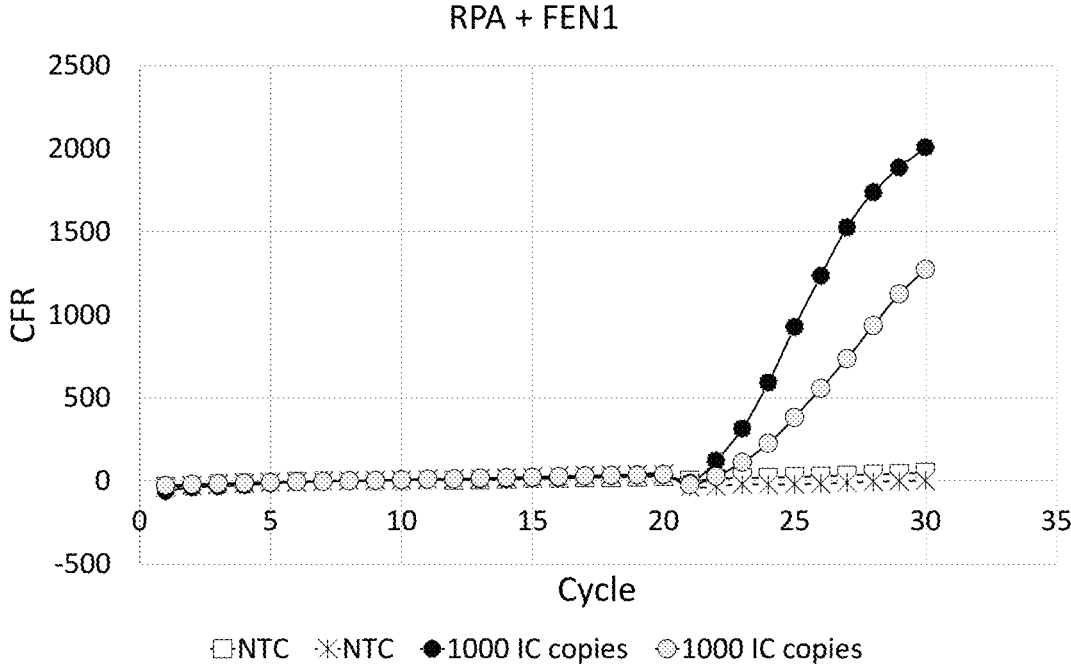
FIG. 23 illustrates an experiment where an RT-RPA reaction and a FEN1 cleavage detection reaction were carried out within the same vessel or tube by combining all RT, RPA, and FEN1 cleavage reaction reagents together with the target nucleic acid.

The RT-RPA was performed for 10 minutes at 42° C. Following amplification, the reaction was brought to 95° C. for as little as 1 second (denaturation step) before the fluorescence signal was detected at 63° C., indicating the presence of the amplified product. Intervals at which the fluorescence was read during amplification and detection were 30 seconds in length (each cycle is 30 seconds). The fluorescence signal was detected starting at around 20 cycles in the samples containing $2 \times 10^3$ copies of the target transcript (FIG. 23).

Sequences:
RdRp Assay
RT-RPA Primers:
RDRP-nCoV-R1 (reverse primer)

(SEQ ID NO: 1)
5'-GACAGCTTGACAAATGTTAAAAACACTATTAGCATA-3'

RDRP-nCoV-F1 (forward primer)

(SEQ ID NO: 2)
5'-TATTGAGTGAAATGGTCATGTGTGGCGGTTCA-3'

FEN1 Cleavage Detection Reaction Oligos:
nCov_IO_2 (initiator oligo)

(SEQ ID NO: 3)
5'-AGCAGTTGTGGCATCTCCTGATGAT-3' nCov_IO_IP_2 (FEN1 probe)

(SEQ ID NO: 4)
5'- CTGGGCTCTACGACCGGTTCCACCTGGTTTAACATATAG-3'

INV-URA-2 (FEN1 reporter)

(SEQ ID NO: 5)
5'-BHQ1-AGCG[T-FAM]GCAGGTGCGGAGTAGAGCCGCACCTGCACG

CGGTCGTAGAGCCCAGAACGA-3'

N3 Assay:
RT-RPA Primers:
N3_F1 (forward primer)

(SEQ ID NO: 6)
5'-CAACTTCCTCAAGGAACAACATTGCCAAAA-3'

N3_R1 (reverse primer)

(SEQ ID NO: 7)
5'-TGGAGTTGAATTTCTTGAACTGTTGCGACT-3'

-continued

FEN1 Cleavage Detection Reaction Oligos:
N3_IO_2 (initiator oligo)

(SEQ ID NO: 8)
5'-CGTGATGAGGAACGAGAAGAGGCTTGACTGCCGCCTA-3'

-continued

N3_IO_IP_2 (FEN1 probe)

(SEQ ID NO: 9)
5'-GTTCTGGGCTCTACGACCCTGCTCCCTTCTGCGTAG-3'

INV-URA-2 (FEN1 reporter)

(SEQ ID NO: 10)
5'-BHQ1-AGCG[T-FAM]GCAGGTGCGGAGTAGAGCCGCACCTGC

ACGCGGTCGTAGAGCCCAGAACGA-3'

Internal control (IC11 N3 Assay)
Template sequence:

(SEQ ID NO: 11)
5'-CAACUUCCUCAAGGAACAACAUUGCCAAAACGUGCGUAGCGAAUAG

UGUAGGUGGUGCGACGGAAUACGAUGCGUGAGCACAGCAGAGCGUAUGG

GCAUAAAGUGGUGGCACAGUGAAUGGCACUGAGCGAGUCGCAACAGUUC

AAGAAAUUCAACUCCA-3'

FEN1 Cleavage Detection Reaction Oligos:
1011 IO_IP_2C (to be used with IC11 RPA R-1)(FEN1
probe)

(SEQ ID NO: 12)
5'-TCGATACAGGGTCCACGTTATGCCCATACGCTCTGC-3'

IC11 RPA R-1 (initiator oligo)

(SEQ ID NO: 13)
5'-CGCTCAGTGCCATTCACTGTGCCACCACTT-3'

INV-UR C-1 (FEN1 reporter)

(SEQ ID NO: 14)
5'-BHQ2-AGCG[T-CFR]GCAGGTGCGGAGTAGAGCCGCACCTGCAC

GCCGTGGACCCTGTATCGAGCA-C3 spacer-3'

Oligonucleotide sequences for the SDA reaction
RdRP-R2-SDA (reverse primer)

(SEQ ID NO: 15)
5'-CGATTCCGCAATGCGAGTCGAGGCAAATGTTAAAAACACTATTAG

CATA-3'

RdRP-F2-SDA (forward primer)

(SEQ ID NO: 16)
5'-ACCGCATCGAATGCGAGTCGAGGGTGAAATGGTCATGTGTGGCGG-3'

-continued

Bumper-R1 (reverse bumper primer)

(SEQ ID NO: 17)

5'-GGCCGTGACAGCTTGA-3'

Bumper-F1 (forward bumper primer)

(SEQ ID NO: 18)

5'-GCTAATGAGTGTGCTCAAGT-3'

RPA + FEN1 in one tube reactions

1C11 RPA F-1

(SEQ ID NO: 19)

5'-CGTGCGTAGCGAATAGTGTAGGTGGTGCGA-3'

-continued

IC11 RPA R-1

(SEQ ID NO: 20)

5'-CGCTCAGTGCCATTCACTGTGCCACCACTT-3'

IC11 IO_IP_2C_C3

(SEQ ID NO: 21)

5'-TCGATACAGGGTCCACGTTATGCCCATACGCTCTGC-C3-3'

IC11 N3_IO_IP_4a (SEQ ID NO: 22)

5'-TCGATACAGGGTCCACGTCGCTCAGTGCCATTCA-C3-3'

---

What is claimed is:

1. A method for detecting presence of a target nucleic acid in a sample, comprising:

amplifying the target nucleic acid via a recombinase polymerase amplification (RPA) reaction at 42° C. or less that generates amplicons, wherein the RPA reaction comprises one or more RPA proteins, a forward primer, a reverse primer, and a strand displacing polymerase; and detecting the generated amplicons via a FEN1 cleavage detection reaction, wherein the FEN1 cleavage detection reaction uses FEN1 cleavage detection reagents that are added after the RPA reaction, and wherein the FEN1 cleavage detection reagents comprise an initiator oligonucleotide, a FEN1 probe oligonucleotide, a FEN1 endonuclease, and a FEN1 reporter oligonucleotide, which are used in two successive steps:

a first step comprising deactivating the RPA proteins at about 95° C., binding of the initiator oligonucleotide and the FEN1 probe oligonucleotide to the target nucleic acid, and cleaving off a detection flap of the FEN1 probe oligonucleotide, and a second step comprising binding of the detection flap from the first step to the FEN1 reporter oligonucleotide, and wherein the binding of the detection flap to the FEN1 reporter oligonucleotide generates a fluorescent signal indicative of the presence of the target nucleic acid in the sample.

2. The method of claim 1, wherein the target nucleic acid is an RNA-dependent RNA polymerase (RdRP) gene.

3. The method of claim 1, wherein the target nucleic acid is associated with a disease.

4. The method of claim 3, wherein the disease is COVID-19.

5. The method of claim 1, wherein the target nucleic acid is a gene or fragment thereof from a virus.

6. The method of claim 5, wherein the virus is SARS-COV-2.

7. The method of claim 1, further comprising a denaturing step that includes deactivating the RPA proteins.

8. The method of claim 1, wherein the RPA proteins comprise at least one recombinase enzyme selected from the group consisting of uvsX recombinase, RecA, RadA, and Rad51.

9. The method of claim 1, wherein the RPA proteins comprise at least one DNA binding protein selected from the group consisting of gp32, a bacterial single-strand binding protein (SSB), and replication protein A.

10. The method of claim 1, wherein the RPA proteins comprise a recombinase loading protein selected from the group consisting of uvsY, RecOR, and Rad52.

11. The method of claim 1, wherein the forward primer comprises SEQ ID NO: 2 and the reverse primer comprises SEQ ID NO: 1, or the forward primer comprises SEQ ID NO: 6 and the reverse primer comprises SEQ ID NO: 7.

12. The method of claim 1, wherein the RPA reaction comprises a reverse transcriptase.

13. The method of claim 1, wherein the FEN1 initiator oligonucleotide comprises SEQ ID NO: 3, SEQ ID NO: 8, SEQ ID NO: 13, or a combination thereof.

14. The method of claim 1, wherein the FEN1 probe oligonucleotide comprises SEQ ID NO: 4, SEQ ID NO: 9, SEQ ID NO: 12, or a combination thereof.

15. The method of claim 1, wherein the FEN1 probe oligonucleotide comprises SEQ ID NO: 5, SEQ ID NO: 10, SEQ ID NO: 14, or a combination thereof.

16. A method for detecting the presence of a target nucleic acid in a sample, comprising:

a. mixing the sample, RPA reaction reagents, and FEN1 cleavage detection reaction reagents together in a vessel, the RPA reaction reagents comprising RPA proteins, b. amplifying the target nucleic acid via the RPA reaction at 42° C. or less thereby generating amplicons, and c. detecting the generated amplicons via a FEN1 cleavage detection reaction, wherein the FEN1 cleavage detection reaction comprises using an initiator oligonucleotide, a FEN1 probe oligonucleotide, a FEN1 endonuclease, and a FEN1 reporter oligonucleotide in two successive steps, d. deactivating the RPA proteins at about 95° C., binding of the initiator oligonucleotide and the FEN1 probe oligonucleotide to the target nucleic acid, and cleaving off a detection flap of the FEN1 probe oligonucleotide, and e. binding of the detection flap to the FEN1 reporter oligonucleotide, and wherein the binding of the detection flap to the FEN1 reporter oligonucleotide generates a fluorescent signal indicative of the presence of the target nucleic acid in the sample, and wherein the amplifying and detecting are performed within the same vessel.

17. The method of claim 16, wherein the RPA reaction reagents comprise a forward primer, a reverse primer, and a strand displacing polymerase, and the FEN1 cleavage detection reaction comprises a FEN1 enzyme, a FEN1 probe oligonucleotide, and a FEN1 reporter oligonucleotide.

18. The method of claim 17, wherein the FEN1 probe oligonucleotide is blocked by one of phosphorylation, a C3 spacer, or an inverted dT at the 3' end.

19. The method of claim 17, wherein the FEN1 probe oligonucleotide includes one or more base pair mismatches.

20. The method of claim 16, wherein an RPA primer is used as an initiator oligonucleotide for the FEN1 cleavage detection reaction.

21. The method of claim 16, wherein the method further comprises a reverse transcription reaction.

22. The method of claim 21, wherein reagents for the reverse transcription reaction are added during step (a).

23. The method of claim 21, wherein the reverse transcription reaction is carried out within the same vessel as the RPA reaction and FEN1 cleavage detection reaction.

24. The method of claim 16, wherein the target nucleic acid is a gene or fragment thereof from a virus.

25. The method of claim 24, wherein the virus is SARS-COV-2.

26. The method of claim 16, wherein the target nucleic acid is associated with a disease.

27. The method of claim 26, wherein the disease is COVID-19.

28. The method of claim 16, wherein the FEN1 cleavage detection reaction occurs at a temperature between 58° C. and 70° C.

* * * * *